United States Patent [19]

Wei et al.

[11] Patent Number: 4,537,969
[45] Date of Patent: Aug. 27, 1985

[54] IMIDAZOLE DERIVATIVES

[75] Inventors: Chung-Chen Wei, Cedar Knolls; Manfred Weigele, North Caldwell, both of N.J.

[73] Assignee: Hoffmann-La Roche Inc., Nutley, N.J.

[21] Appl. No.: 568,329

[22] Filed: Jan. 5, 1984

Related U.S. Application Data

[62] Division of Ser. No. 359,326, Mar. 18, 1982, Pat. No. 4,431,653.

[51] Int. Cl.$^3$ .................. C07D 277/08; A61K 31/415
[52] U.S. Cl. .................... 546/210; 548/336; 260/245.2 R; 260/245.2 T
[58] Field of Search ................. 260/245.2 R; 548/346, 548/336; 546/210

[56] References Cited

U.S. PATENT DOCUMENTS

| | | | |
|---|---|---|---|
| 3,255,588 | 8/1973 | Lund | 424/251 |
| 4,076,816 | 2/1978 | Tybring | 424/251 |
| 4,089,963 | 5/1978 | Bamberg et al. | 424/270 |
| 4,229,443 | 10/1980 | Binderup | 424/200 |
| 4,241,060 | 12/1980 | Smithen et al. | 546/210 |
| 4,246,262 | 1/1981 | Vangedal | 424/244 |

OTHER PUBLICATIONS

Abstract, Derwent 54846Y/31 Japan J5 2073-890, Yoshitomi (I), Dec. 18, 1975.
Abstract, Derwent 38818C/22 Great Britain GB 2031-879, Tarchomin, Apr. 30, 1980.
Abstract, Derwent 61863Y/35 Japan J5 2085-186, Yoshitomi (II), Jul. 15, 1977.

*Primary Examiner*—Nicholas S. Rizzo
*Attorney, Agent, or Firm*—Jon S. Saxe; Bernard S. Leon; George W. Johnston

[57] ABSTRACT

6-Amidinopenicillanic acid derivatives wherein one of the nitrogen atoms of the amidino group is part of a heterocyclic ring having on a side chain an unsubstituted heterocyclic ring containing 2 to 3 nitrogen atoms, and being useful as an antibiotic.

6 Claims, No Drawings

IMIDAZOLE DERIVATIVES

This is a division of application Ser. No. 359,326 filed Mar. 18, 1982 now U.S. Pat. No. 4,431,653.

SUMMARY OF THE INVENTION

In accordance with this invention, it has been discovered that penicillanic acid derivatives of the formula:

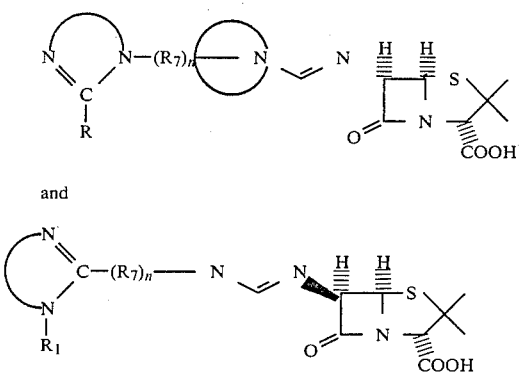

wherein n is an integer from 0 to 1;

is a saturated 5 to 7 membered heterocyclic ring containing the one nitrogen atom as the only hetero atom in said ring, said ring being unsubstituted or substituted in one or more positions with lower alkyl;

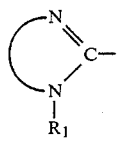

is a 5 to 7 membered heterocyclic ring which contains no additional double bond or can also be aromatic when it is 5-membered, said ring being either unsubstituted or substituted in one or more positions with lower alkyl; $R_1$ is hydrogen or lower alkyl;

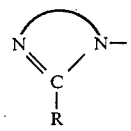

is a 5 to 7 membered heterocyclic ring having at most one additional nitrogen atom as the only hetero atom, from 0 to two additional double bonds and, aside from R, either being unsubstitted or substituted in one or more positions with a lower alkyl group; R is selected from the group consisting of lower alkyl, nitro, hydrogen, —COOH, —(CH$_2$)$_y$—NHR$_4$, —(CH$_2$)$_y$OR$_3$ and

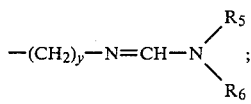

$R_3$ is hydrogen, or lower alkyl, y is an integer from 0 to 4; $R_4$ is hydrogen, lower alkyl, or an amino protecting group; $R_5$ and $R_6$ are hydrogen or lower alkyl, and $R_7$ is lower alkylene;

and/or salts of said compounds I and II; or hydrolyzable esters or hydrates thereof are useful in treating infectious diseases caused by bacterial microorganisms such as *K. pneumoniae, E. coli, E. cloacae, P. aeraginosa, P. vulgaris,* and *S. marcescens.*

DETAILED DESCRIPTION

The term "lower alkyl" designates monovalent saturated straight or branched aliphatic hydrocarbon groups containing from 1 to 7 carbon atoms such as ethyl, methyl, n-propyl, isopropyl, n-butyl, isobutyl, tert-butyl, with methyl and ethyl being preferred. The term "lower alkylene" designates a divalent saturated aliphatic straight or branched chain hydrocarbon radical containing from 1 to 7 carbons such as methylene, isopropylene, ethylene, etc. The term "halogen includes all four halogens such as chlorine, bromine, fluorine and iodine with chlorine and bromine being preferred. The term "lower alkanoyl" designates alkanoyl groups derived from aliphatic monocarboxylic acids containing from 1 to 7 carbon atoms such as acetyl, propionyl, butyryl, pivaloyl, etc.

The ring

is a saturated 5 to 7 membered heterocyclic ring containing the one nitrogen atom as the only hetero atom in the ring. This ring can be unsubstituted or substituted in one or more positions with a lower alkyl group preferably methyl or ethyl. Generally, 6 to 7 membered rings are preferred with a 6 membered ring being especially preferred. If the ring is substituted, it is generally preferred that the ring be substituted at one or two positions with a lower alkyl group preferably methyl or ethyl. The ring systems designated by

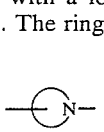

is most preferably piperidyl.

The ring system

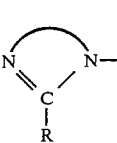

designates a 5 to 7 membered heterocyclic ring. This ring can contain additional nitrogen hetero atoms. Preferably, this ring system contains only two nitrogen atoms and from 5 to 6 members. However, ring systems containing 3 nitrogen atoms can be used in the penicillanic acid derivative of this invention. The carbon atoms other than the carbon atom separating the two nitrogen atoms in the ring can be unsubstituted or substituted with a lower alkyl group, preferably methyl or ethyl. The carbon atom separating the two nitrogen atoms in the ring can be substituted with any substituent designated by R. This ring system contains a double bond between the carbon separating the two nitrogen atoms in the ring and one of these nitrogen atoms. In addition, this ring system can contain no other double bonds or can contain one or two additional double bonds. Among the preferred ring systems are:

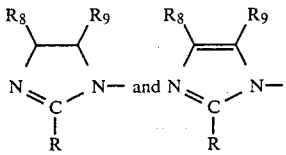

where $R_8$ and $R_9$ are hydrogen or lower alkyl, preferably methyl or ethyl; and R is as above.

The ring system

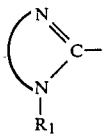

is a 5 to 7 membered heterocyclic ring system containing the two nitrogen atoms as the only hetero atom in the ring system. Generally, it is preferred that this ring system contain five or six members. This ring system can contain only one double bond or can be completely unsaturated, i.e. aromatic. The preferred rings designated by the substituent are:

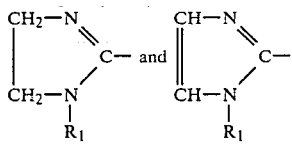

When $R_4$ in the compound of formula I is an amino protecting group, any conventional amino protecting group can be utilized in the compounds of this invention. Any of the conventional amino protecting groups which can be removed by conventional acid hydrolysis or catalytic hydrogenation are preferred for use in the compounds of this invention. Among the preferred amino protecting groups are included trityl, benzyloxycarbonyl, o-nitrophenylsulphenyl, t-butoxycarbonyl, benzyl, diphenylmethyl, etc.

The salts of the compounds of the invention are in addition to their inner salts (zwitterions) mono- or dibasic salts, formed with non-toxic, pharmaceutically acceptable acids. Among these acids are included hydrochloric acid, phosphoric acid, nitric acid, p-toluenesulphonic acid, acetic acid, propionic acid, citric acid, tartaric acid, maleic acid etc. In addition to these acids, any conventional pharmaceutically acceptable, non-toxic inorganic or organic acids can be used to form the salts of the compounds of formulae I and II. These salts can be prepared by treating the compounds of formulae I and II with the aforementioned acids by conventional means well known in the art.

Also included in the invention are salts with pharmaceutically acceptable, non-toxic, inorganic or organic bases, e.g. alkali metal salts and alkaline earth metal salts, for example sodium, potassium, magnesium or calcium salts, as well as salts with ammonia or suitable non-toxic amines, such as lower alkyl amines, for example triethylamine, hydroxy-lower alkylamines, for example 2-hydroxyethylamine, bis-(2-hydroxyethyl)amine or tris-(2-hydroxyethyl)-amine, cycloalkylamines, for example dicyclohexylamine, or benzylamines, for example N,N'-dibenzyl-ethylenediamine, and dibenzylamine. Thus for instance other antibiotics with acid or basic character can be used as components of such salts of the compounds of formulae I and II.

The salts can also be hydrated either during manufacture or by gradual hydration of an initially anhydrous salt due to the hydroscopic properties of the compounds of formulae I and II above.

The hydrolyzable, pharmaceutically acceptable esters of the compounds of formulae I and II are the well known types of easily hydrolyzable esters, e.g. lower alkanoyl esters, acyloxyalkyl esters, such as lower alkanoyloxyalkyl esters, e.g. acetoxymethyl and pivaloyloxymethyl esters and the corresponding 1-acetoxyethyl and 1-pivaloyloxyethyl esters, alkoxycarbonyloxyalkyl esters, e.g. methoxycarbonyloxymethyl and 1-ethoxycarbonyloxyethyl esters, lactonyl esters, e.g. phthalidyl esters, or lower alkoxymethyl and acylaminomethyl esters. Other acyloxyalkyl esters are within the scope of the invention, e.g. such esters in which the acyl group is a radical derived from a beta-lactam antibiotic, such as a penicillin, cephalosporin, an amidinopenicillanic acid or clavulanic acid, which esters when hydrolyzed in the host may give rise to enhanced effect. Also other esters can be useful, e.g. the benzyl ester and the cyanomethyl ester.

Appropriately the esters above can be prepared and used in the form of their salts with pharmaceutically acceptable, non-toxic inorganic or organic acids or bases.

A series of substituted 6-beta-amidinopenicillanic acids, their salts and easily hydrolyzable esters are disclosed in the British Pat. No. 1,293,590 and other easily hydrolyzable esters of the compounds of British Pat. No. 1,293,590 have been disclosed in the British Pat. Nos. 1,335,718 and 1,405,886.

Among the pharmaceutically acceptable, non-toxic esters of the amidopenicillanic acid derivatives of formulae I and II are included the diesters of the formula:

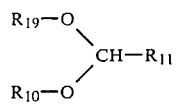

wherein $R_{19}$ is the acyl radical of one of the compounds of formulae I and II; $R_{10}$ is the acyl radical of one of the compounds of formulae I and II or an acyl radical of another known beta-lactam antibiotic; and $R_{11}$ is hydrogen, lower alkyl, or phenyl or salts of such esters with pharmaceutically acceptable non-toxic acids or bases.

The compounds of formulae I and II, their salts and their hydrolyzable esters are effective in the treatment of infectious disorders caused by gram positive and gram negative bacterial microorganisms such as *K. pneumoniae, E. coli, E. cloacae, P. aeruginosa, P. vulgaris* and *S. marcescens.*

It is also an object of the present invention to provide an antibacterial pharmaceutical composition for use in the treatment of infectious diseases, which contains as an active ingredient a 6-aminopenicillanic acid derivative of the formulae I, II, or III given hereinbefore.

For parenteral and topical use, the compounds of formulae I, II and III or their salts are preferred. These can also in some cases be used orally. However, for oral use it is in most cases advantageous to use an easily hydrolyzable ester of the compounds, because such esters are generally better absorbed than the corresponding acids or salts. The esters have no antibacterial activity per se, but they are during or after the absorption hydrolyzed to liberate the corresponding free acids.

The active ingredient can be used as such or can be mixed up with a carrier and/or an auxiliary agent.

In such compositions, the proportion of therapeutically active material to carrier substance and auxiliary agent can vary between 1% and 95% by weight. The compositions can either be in any conventional pharmaceutical form such as tablets, pills or dragees, or can be filled in medical containers such as capsules, or as far as suspensions are concerned filled into bottles. Pharmaceutical organic or inorganic solid or liquid carriers suitable for enteral, parenteral or topical administration can be used to make up the composition. Gelatine, lactose, starch, magnesium stearate, talc, vegetable and animal fats and oils, gum, polyalkylene glycol, or other known carriers for medicaments may all be suitable as carriers.

In the pharmaceutical compositions, the compounds of the invention can be used together with other suitable therapeutically active components, preferably with other antibacterially active compounds, such as beta-lactam antibiotics, e.g. penicillins or other aminopenicillanic acid derivatives, and cephalosporins. Also other antibacterially active substances are of interest in this connection, e.g. aminoglycosides. In combinations with beta-lactam antibiotics such as penicillins like ampicillin, amoxicillin, or carbenicillin, or cephalosporins like cephalothin, cefazolin or cephalexin, a synergistic effect is observed which is of importance in many clinical situations. Also a depression of development of resistance can be obtained by a combination therapy. In such compositions, the weight ratio between the active components appropriately is between 1:20 and 20:1, preferably within the ratio 1:5 and 5:1. These active components may be administered together or the compounds of this invention may be administered before of after the administration of another beta-lactam antibiotic.

The compounds of the invention can also be used together with a beta-lactamase inhibitor, such as clavulanic acid. Another object of the invention resides in the selection of a dose for the compounds of the invention which can be administered so that the desired activity is achieved without simultaneous secondary effects.

The compounds of this invention alone or in combination with other beta-lactam antibiotics can be conveniently administered orally in dosage units amounts corresponding to from 0.025 g to 2.5 g of these compounds, preferably from 0.05 g to 1.5 g depending on which microorganisms are involved. By the term "dosage unit" is meant a unitary, e.g. a single dose capable of being administered to a patient, and which may be readily handled and packed, remaining as a physically stable unit dose, comprising either the active material as such or a mixture of it with a pharmaceutical carrier. Generally, the oral dosage units are administered in accordance with the patient's needs, preferably from 2 to 8 times a day and most preferably from 2 to 6 times a day.

Similarly, for infusion, the compounds of the invention are given in doses up to 10 mg in aqueous solution.

For parenteral use, e.g. injections, the compounds of the invention or in combination with other beta-lactam antibiotics are given e.g. in an aqueous solution or suspension as a dosage unit containing from 0.1 g to 2.5 g of these active compounds to be dissolved or suspended immediately before use, or ready for use together with a pharmaceutically acceptable vehicle. In the form of a dosage unit these active compounds may be administered once or more times a day at appropriate intervals, always depending, however, on the condition of the patient. As used herein the term "patient" includes animals as well as humans. Thus, a daily dose will preferably amount to from 0.2 g to 20 g of the compounds of the invention alone or together with other beta-lactam antibiotics with daily amounts of from 1 to 12 grams parenterally administered being especially preferred.

The compounds of the invention are appropriately administered in the form of their pharmaceutically acceptable, non-toxic, easily hydrolyzable esters.

The compounds of formulae I and II and their salts, esters and hydrates when administered together or in combination with other beta-lactam antibiotics such as cephalosporins and penicillins exhibit enhanced antibacterial properties due to this combination. In general, effects are achieved through the use of these combinations. In preparing a dosage unit for oral, topical or parenteral use, the weight ratio between the active ingredients in a combination can vary between 1 to 20 parts of an antibiotic of formulae I or II and from 20 to 1 parts of another beta-lactam antibiotic.

The term "non-toxic" for easily hydrolyzable esters shall mean that such esters are therapeutically acceptable for their intended form of administration. In general the easily hydrolyzable esters of the compounds of the invention are used in the oral administration, but their use in the parenteral administration is also within the scope of the invention.

The compounds of formulae I and II are prepared by reacting a compound of the formula:

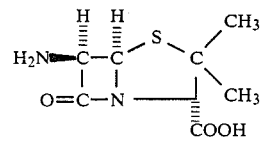

or hydrolyzable esters or salts thereof
with a compound of the formula:

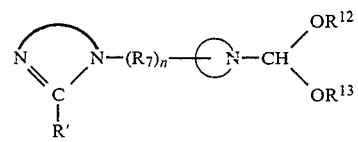

wherein $R_7$ and n are as above, R' is the same as R except that the substituents designated by R containing free amino groups are in their protected form; $R^{12}$ and $R^{13}$ are lower alkyl or taken together form —$CH_2$—$(CH_2)_x$—$CH_2$— wherein x is an integer from 0 to 2
or a compound of the formula

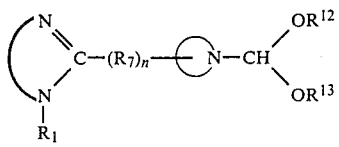  VI wherein n, $R_7$, $R_1$, $R_{12}$ and $R_{13}$ are as above.
When $R_{12}$ and $R_{13}$ are lower alkyl groups, these substituents are selected from the same group.

The reaction of the compound of formula IV with either a compound of formula V or compound of formula VI can be carried out in an organic solvent medium in the presence of a tertiary amine base. In carrying out this reaction, any conventional inert organic solvent can be utilized. Among the preferred organic solvents are included methylene chloride, chloroform, as well as other halogenated hydrocarbons. Furthermore, in carrying out this reaction, any conventional tertiary amine base can be utilized. Among the conventional tertiary amine bases that can be utilized are included trimethylamine, triethylamine, N,N-diisopropyl ethylamine, or N-methylmorpholine. In carrying out this reaction, temperature and pressure are not critical and the reaction can be carried out at room temperature and atmospheric pressure. If desired, higher or lower temperatures can be utilized.

If desired, the compounds produced by the reaction of compounds of formula IV with either the compound of formula V or VI, which contain a protected amine substituent can be converted into the free amine by mild acid hydrolysis. Any conventional method of mild acid hydrolysis can be utilized to convert these reaction products to the compound of formula I containing the free amino substituent. On the other hand, the compound of formula I where R is a nitro group can be converted to the corresponding compound of formula I where R is $NH_2$ by reduction such as hydrogenation. Any conventional method of hydrogenating a nitro substituent to an amine can be utilized in carrying out this conversion.

On the other hand, the reaction products of either the compound of formulae V and VI with the compound of formula IV where the carboxyl group is protected by an ester substituent can be converted to the corresponding compounds of formulae I and II which contain free carboxyl groups by mild basic hydrolysis or hydrogenolysis. Any conventional method of basic hydrolysis or hydrogenolysis can be utilized to produce the free acid of compounds of formulae I and II. If the compound of formula I and II is produced as the free acid, this compound can be esterified by any conventional means.

The compound of formula V is prepared in accordance with this invention by first reacting a compound of the formula

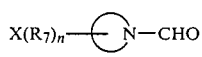  VII wherein X is a halogen or a leaving group and $R_7$ and n are as above
with a compound of the formula

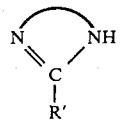  VIII where R' is as above
to produce a compound of the formula

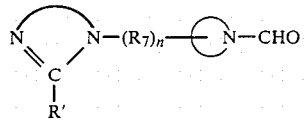  IX wherein $R_7$, R' and n are as above.
The compound of formula IX is then converted to a compound of the formula:

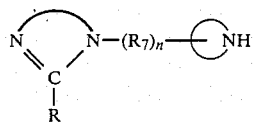  X wherein $R_7$, R and n are as above
or a salt thereof which is then reacted with a compound of the formula:

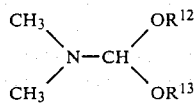  XI wherein $R^{12}$ and $R^{13}$ are as above
to produce the compound of formula V.

The reaction of the compound of formula VII with the compound of formula VIII to produce a compound of the formula IX is carried out in the presence of a base and an organic solvent. Any conventional inert organic solvent can be utilized in carrying out this reaction. Among the preferred solvents are dimethylformamide, ethyl alcohol, dimethylsulfoxide, etc. In carrying out this reaction, any strong base can be utilized. Among the preferred bases are included sodium carbonate, sodium hydride, with sodium hydride being especially preferred. Generally it is preferred to carry out this reaction at a temperature of from 70° C. to 150° C. In the compound of formula VII, X can be any conventional leaving group with mesyloxy or tosyloxy being preferred. On the other hand X can be a halide such as chloride or bromide.

The compound of formula IX is converted to the compound of formula X by treating the compound of formula IX with aqueous inorganic acid such as hydrochloric acid at elevated temperatures. This reaction can be carried out in the presence of an organic solvent. Any conventional inert organic solvent can be utilized in carrying out this invention. Among the preferred inert organic solvents are included dioxane, tetrahydrofuran, etc., with dioxane being especially preferred. In carrying out this reation, temperatures from about 80° C. to 120° C. are generally utilized with the reflux temperature being preferred. The use of an acid produces the compound of formula IX in the form of its salt which, if desired, can be neutralized with a base to form the free base of the compound of formula IX. Either the compound of formula IX in the form of its salt or as a free base can be utilized in the subsequent reactions to produce the compound of formula V.

Alternatively, the compound of formula IX can be converted to the compound of formula X by treating the compound of formula IX with an organic aqueous alkali metal hydroxide in a lower alkanol solvent. In carrying out this reaction, temperatures of from 30° C. to 50° C. are utilized. Where $R^1$ in the compound of formula IX contains an amino group protected by means of a amino protecting group removable by acid hydrolysis such as trityl or tert-butoxy carbonyl, it is preferred to convert the compound of formula IX to the compound of formula X by treatment with an alkali metal hydroxide rather than an aqueous inorganic acid since treatment with an inorganic acid hydrolizes the amino protecting group.

If one treats the compound of formula IX where R' contains an amino protecting group with an inorganic acid to produce the compound of formula X, it is necessary to protect the free amino group again to carry out the further reactions to produce the compound of formula V. Where R' is converted to a free amino group in the compound of formula X, the compound of formula X contains both a primary and secondary amine group. Therefore, care must be taken in protecting the primary amino group in the compound of formula X so as not to protect the secondary amino group. This can be done by conventional means since the primary amino group reacts first with compounds such as trityl chloride before the less reactive secondary amino group. In this manner, the compound of formula X is produced having its secondary amino group free and ready for further reaction.

Compounds of formula IX where R' is hydrogen can, if desired, be converted to the corresponding compounds of formula IX where R' is —CH$_2$OH by reacting the compound of formula IX where R' is hydrogen with aqueous formaldehyde at temperatures of 120° to 200° C. in an autoclave. The compound of formulae IX and X where R' is —CH$_2$OH can be converted, if desired, to the corresponding compounds of formulae IX and X where R' is —COOH by oxidation. Any conventional method of oxidizing an alkanol to an acid such as by use of oxidizing agents such as potassium permagnate can be used in carrying out this reaction.

If R' in the compound of formulae IX or X is nitro, this compound can be converted to the corresponding compound of formula IX or X where R' is —NH$_2$ by hydrogenation such as described hereinbefore. This amino group can be protected in the manner described hereinbefore. On the other hand, the amino protecting group can, if desired, be removed by conventional means from the compound of formula X.

The reaction of the compound of formula X with a compound of formula XI to produce the compound of formula V is carried out at temperatures from 70° to 110° C. In carrying out this reaction, the compound of formula XI may be utilized as the reaction medium. If desired, other conventional inert organic solvents may be present in this reaction medium. If the compound of formula X contains a free amino group, i.e. the compound of formula X where R is —(CH$_2$)$_y$NH$_2$, this reaction produces the compound of formula V where R' is

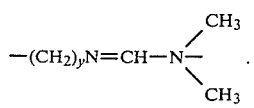

On the other hand, the compound of formula IX where R' is lower alkyl or hydrogen can be prepared by reacting a compound of the formula:

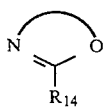   XII wherein $R_{14}$ is hydrogen or lower alkyl; and the ring

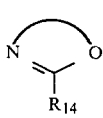

designates a 5 to 7 membered heterocyclic ring having at most one additional nitrogen as the only hetero atom and from 0 to 2 additional double bonds with a compound of the formula

   XIII wherein R$_7$ and n is as above at a temperature of from 120° to 150° C. This reaction is generally carried out in the presence of catalytic amounts of a lower alkanoic acid with formic acid, acetic acid or propionic acid being preferred. In carrying out this reaction, no solvent is utilized and the reaction is carried out by heating the compound of formula XII with the compound of formula XIII to a temperature of from 120° C. to 150° C. in the presence of catalytic amounts of a lower alkanoic acid containing from 1 to 7 carbon atoms.

The compounds of formula VII are known compounds. In accordance with a preferred embodiment of this invention the compound of formula VII where n is 1 can be prepared from compounds of the formula

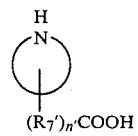   XIV where R$_7$' is a lower alkylene containing from 1 to 6 carbon atoms, and n' is 0 to 1 via the following intermediates

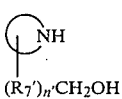   XV

-continued

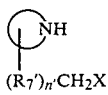   XVI

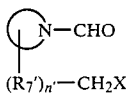   VII-B wherein n', R₇' and X are as above and the ring

is as above.

The compound of formula XIV is converted to the compound of formula XV by reduction. Any conventional method of reducing a carboxyl group to the corresponding hydroxy group can be utilized to carry out this reaction. In accordance with a preferred embodiment of this invention, the compound of formula XIV is treated with diborane in an inert organic solvent such as tetrahydrofuran. Any of the conventional conditions utilized in reducing with diborane can be utilized to carry out this reaction. The compound of formula XV is converted into the compound of formula XVI by treating the compound of formula XV with a halogenating agent such as a phosphorus trihalide especially phosphorus tribromide or a compound capable of yielding a leaving group such as tosyl chloride or mesyl chloride. In carrying out this reaction any of the conditions conventional in such reactions can be utilized in this procedure.

The compound of formula XVI is converted to the compound of formula VII-B by treating the compound of formula XVI with acetic formic anhydride in the presence of a tertiary amine. Any of the conventional tertiary amines such as those hereinbefore mentioned can be utilized in carrying out this invention. Generally this reaction is carried out at temperatures of from −10° to +10° C. with 0° C. being especially preferred.

The compound of formula VI is prepared from a compound of the formula

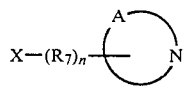   XVII wherein R₇, n and X are as above and the ring

is either an aromatic or saturated 5 to 7 membered heterocyclic ring containing the nitrogen atom as the only hetero atom in the ring and being unsubstituted or substituted in one or more positions with lower alkyl
via the following intermediates

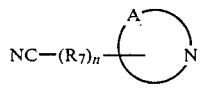   XVIII

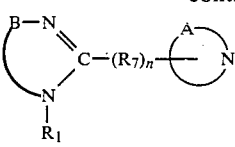   XIX

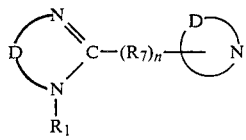   XIX-A

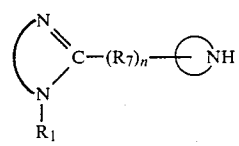   XX wherein R₇, R₁, and n are as above and the rings

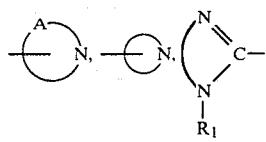

are as above and the ring

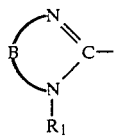

designates a 5 to 7 membered heterocyclic ring which contains no additional double bonds and unsubstituted or substituted in one or more positions with lower alkyl;

designates a 5 to 7 membered aromatic heterocyclic ring containing the nitrogen atom as the only hetero atom in the ring and being unsubstituted or substitued in one or more positions with lower alkyl; and R₁ is as above.

The compound of formula XVII is converted to the compound of formula XVIII by utilizing any conventional method of converting a halide or a leaving group to a cyanide functional group. Among the preferred methods which can be utilized is by reacting the compound of formula XVIII with an alkali metal cyanide such as sodium cyanide. Any of the conditions conventional in carrying out this reaction can be utilized.

In converting the compound of formula XVIII to the compound of formula XIX, the compound of formula XVIII is reacted with a compound of the formula:

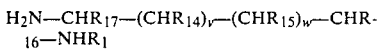   XXI wherein R₁ is as above, R₁₇, R₁₄, R₁₅ and R₁₆ are hydrogen or lower alkyl; and v and w are integers from 0 to 1.

The compound of formula XVIII is reacted with the compound of formula XXI at temperatures of 120° C. to 250° C. in the presence of a strong acid to produce the compound of formula XIX. The preferred acid for utilization in this reaction is paratoluenesulfonic acid. However, any conventional strong acid can be utilized. This reaction produces the compound of formula XIX as a salt. If desired, the compound of formula XIX can be neutralized in an inert organic solvent by the addition of a base such as sodium methoxide to produce the compound of formula XIX as a free base.

If desired, the compound of formula XIX can be converted to the compound of formula XIX-A where both rings are aromatic by treating the compound of formulae XIX with barium manganate or Raney Nickel. If n in the compound of formulae XIX is 1, Raney Nickel and temperatures are from about 200° to about 240° C. are utilized. If n is 0, barium manganate is utilized with temperatures of from 30° C. to 100° C. with temperatures of from about 60° C. to 80° C. being preferred. Reaction of the compound of formula XIX with barium manganate or Raney Nickel aromatizes the ring designated as

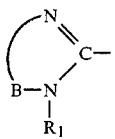

to produce

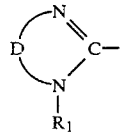

which is the same as the former ring except that it is aromatic.

If the ring

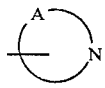

in the compound of formula XIX is an aromatic ring, the compound of formulae XIX and XIX-A can be converted to the compound of formula XX by hydrogenation utilizing a conventional hydrogenation catalyst or platinum oxide. This procedure will hydrogenate this aromatic ring without affecting the double bond between one of the two nitrogen atoms and the carbon which separates them in the ring

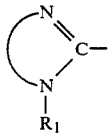

If the latter ring in the compound of formula XIX-A is a five membered ring, this hydrogenation will not affect its aromatic configuration. On the other hand, if this ring is a 6 or 7 membered ring, hydrogenation will affect all double bonds other than the double bond between one of the two nitrogen atoms separated by a carbon atom. In this reduction, the hydrogenation is carried out utilizing conventional hydrogenation conditions, the preferred hydrogenation catalyst being palladium on carbon or platinum. Any of the conventional conditions of hydrogenation can be utilized in carrying out this reaction.

In accordance with another embodiment of this invention, the compound of formula XX or its salt can be prepared from the known compounds of the formula:

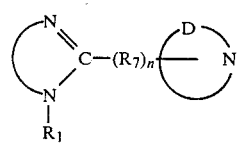

XXII wherein $R_7$, $R_1$, n and the ring

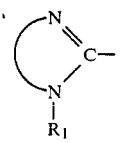

are as above; and the ring

is as above
or its salt by hydrogenation in the same manner as disclosed hereinabove for converting a compound of the formula XIX-A to a compound of formula XX.

The compound of formulae XIX or XX or its salt is converted to the compound of formula VI by reacting the compound of formulae XIX or XX with the compound of formula XI in the same manner described in connection with the reaction of the compound of formula X to produce the compound of formula V.

In accordance with another embodiment of this invention, the compound of formula XIX where

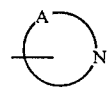

is a saturated ring can be prepared by reacting a compound of the formula:

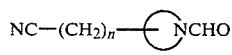

XVIII-A wherein n, and the ring

is as above with the compound of formula XXI in the presence of a strong acid. The same conditions described hereinbefore with regard to the reaction of the compound of formula XXI with a compound of formula XVIII to produce the compound of formula XIX can be used in this reaction.

The following Examples are illustrative but not limitative of the claimed invention. In these Examples, the ether utilized was diethyl ether. The yields in these Examples are given in weight percent. In the Examples, Sephadex LH 20 designates dextran. In the Examples, all temperatures are in degrees Centigrade.

EXAMPLE 1

4-(2-Bromoethyl)-1-piperidinecarboxaldehyde 2-(4-pyridyl)ethanol (70. g, 0.57M) and platinum oxide (2 g) in water (600 ml) and concentrated aqueous HCl (81 ml) was hydrogenated at the pressure of 1000 psig hydrogen to give 4-(2-hydroxyethyl)piperidine hydrochloride in quantitative yield. Treatment of 4-(2-hydroxyethyl)piperidine hydrochloride (20 g 0.12M) with phosphorus tribromide (7 ml) at 100° C. for 1½ hr. followed by trituration with diethyl ether (2×50 ml) and filtration gave 4(2-bromoethyl)piperidine hydrogen bromide (20.76 g, 77% yield). The solution of the 4-(2-bromoethyl)piperidine hydrogen bromide (23 g, 0.085M) in tetrahydrofuran (170 ml) and dimethylformamide (170 ml) was prepared. To this solution was added formic acetic anhydride (12.7 ml) at 0° C., followed by the addition of triethylamine (25 ml) with vigorously stirring. The reaction mixture was stirred overnight. After the reaction, it was filtered and the filtrate was stripped in vacuo to dryness and water (100 ml) was then added to the residue and the mixture was extracted with diethyl ether (3×100 ml). Removal of the solvent and purification on silica gel columns, eluted with ethyl acetate-hexane (9:1 parts by volume) gave 4-(2-bromoethyl)-1-piperidinecarboxaldehyde (12.06 g., 66% yield).

EXAMPLE 2

4-[2-(1H-Imidaz-1-yl)ethyl]piperidine hydrate dihydrochloride

To a mixture of imidazole (4.5 g, 65.8 mM) and sodium hydride (50% by weight in mineral oil, 3.15 g, 66 mM) at 50° C. was added 4-(2-bromoethyl)-1-piperidine carboxaldehyde (12 g, 55 mM) and the reaction was heated at 50° C. for 3 hrs. The solvent was removed in vacuo and water (about 100 ml) was added to the residue and then the mixture was extracted with methylene chloride (3×100 ml). The combined extracts, dried over Na$_2$SO$_4$, were stripped to dryness and purified on silica gel columns, eluted with methanol-methylene chloride (1:9 parts by volume) to give an oil (10.4 g) which was then refluxed with 2N hydrochloric acid (55 ml) in dioxane (400 ml) for 5 hrs. The solvent was removed and the product was crystallized from ethanol diethyl ether yield 4-[2-(1H-imidaz-1-yl)ethyl]piperidine-hydrate-dihydrochloride in overall yield of 55%. 8.2 g of 4-[2-(1H-imidaz-1-yl)ethyl]piperidine-hydrate-dihydrochloride was converted to free base by dissolving in water (100 ml) at pH 11 and extracting with methylene chloride. Evaporation of the methylene chloride extracts in vacuo gave 5.1 g of free base.

EXAMPLE 3

[2S-(2alpha,5alpha,6beta)]-6-[[[4-[2-(1H-Imidazol-1-yl)ethyl]-1-piperidinyl]methylene]amino]-3,3-dimethyl-7-oxo-4-thia-1-azabicyclo[3.2.0]heptane-2-carboxylic acid hydrate hydrochloride The free base 4[2-(imidazol-1-yl)ethyl]piperidine (5.1 g, 28.7 mM) and dimethylformamide dimethyl acetal (23 ml) was heated at 100° C. for 6 hours. Removal of the excess of dimethylformamide dimethyl acetal gave 4-[2-(imidazol-1-yl)ethyl]-1-piperidine carboxaldehyde dimethylacetal (6.32 g, 87%) which was dissolved in CH$_2$Cl$_2$ (27 ml) and added to the mixture of 6-aminopenicillanic acid (5.6 g., 258 mM) and diisopropylethylamine (3.41 ml) in CH$_2$Cl$_2$ (100 ml) at 0° C. The reaction was stirred at 0° C. for 1 hr. and room temperature for 3 hrs. The solvent was then removed and water (100 ml) was added. After being washed with ethylacetate, the aqueous solution, acidified to pH 3, was purified on Sephadex LH 20 columns to give [2-S-(2alpha,5alpha,6beta)]-6-[[[4-[2-(1H-imidazol-1-yl)ethyl]-1-piperidinyl]methylene]amino]-3,3-dimethyl-7-oxo-4-thia-1-azabicyclo[3.2.0]heptane-2-carboxylic acid hydrate hydrochloride (1.8 g, 16% yield).

EXAMPLE 4

4-[(2-Nitro-1H-Imidazol-1-yl)methyl]-1-Piperidinecarboxaldehyde

The mixture of 2-nitroimidazole (4.5 g, 40 mM) and 50% by weight NaH in mineral oil (1.92 g, 41 mM) in dimethylformamide (40 ml) was stirred at room temperature for ½ hr. A solution of 4-bromomethyl-1-piperidinecarboxaldehyde (8.3 g, 40 mM) in dimethylformamide (10 ml) was added to the above mixture and heated at 120° C. for ½ hr. After the reaction, solvent was removed in vacuo and water (50 ml) was added and the mixture was extracted with ethylacetate (2×75 ml). The extracts, dried over Na$_2$SO$_4$ was stripped to dryness which was then purified on silica gel column, eluted with 5% volume MeOH-95% volume CH$_2$Cl$_2$, to give 4[(2-nitro-1H-imidazol-1-yl)methyl]-1-piperidinecarboxaldehyde (2.4 g, 10 mL) in 25% yield.

EXAMPLE 5

[2S-(2alpha,5alpha,6beta)]-3,3-Dimethyl-6-[[[4-[(2-nitro-1H-imidazol-1-yl)methyl]-1-piperidinyl]methylene]amino]-7-oxo-4-thia-1-azabicyclo[3.2.0]-heptane-2-carboxylic acid hydrochloride A mixture containing 4-[(2-nitro-1H-imidazol-1-yl)methyl]-1-piperidinecarboxaldehyde (2.0 g, 8.4 mM) in dioxane (15 ml) and 1 NHCl (15 ml) was heated at 100° C. for 5 hrs. After the reaction, solvent was removed, and the residue, basified with 1N NaOH to pH 10 was extracted with CH$_2$Cl$_2$(3×30 ml). The extracts, dried over Na$_2$SO$_4$, were stripped to give a solid (1.7 g, 8 mM) which was heated with dimethylformamide dimethylacetal (15 ml) in MeOH-CHCl$_3$ (4 ml:15 ml) at 100° C. for 10 hrs. The excess of dimethylformamide dimethylacetal was removed to give 4[(2-nitro-1H-imidazol-yl)-methyl]-piperidinecarboxaldehyde dimethylacetal. This acetal was added at 0° C. to a mixture of 6-aminopenicillanic acid (1.6 g, 7.3 mM) and diisopropylethylamine (1.3 ml) in dry chloroform. The reaction was stirred at 0° C. 1 hr and room temperature for 3 hrs. After the reaction, solvent was removed in vacuo and dissolved in water (40 ml). The aqueous solution, washed with ethyl acetate (2×15 ml), was acidified to pH 3 and purified on Sephadex LH 20 columns to give [2S-(2alpha,5alpha,6beta)]-3,3-dimethyl-6-[[[4-[(2-nitro-1H-imidazol-1-yl)methyl]-1-piperidinyl]-methylene]amino]-7-oxo-4-thia-1-azabicyclo[3.2.0]-heptane-2-carboxylic acid as the hydrochloride salt (0.73 g, 21% yield).

EXAMPLE 6

[2S-(2alpha,5alpha,6beta)]-6-[[[4-[(2-Amino-1H-imidazol-1-yl)methyl]-1-piperidinyl]methylene]amino]-3,3-dimethyl-7-oxo-4-thia-1-azabicyclo[3.2.0]-heptane-2-carboxylic acid hydrochloride The solution of [2S-(2alpha,5alpha,6beta)]-3,3-dimethyl-6-[[[4-[(2-nitro-1H-imidazol-1-yl)methyl]-1-piperidinyl]-methylene]amino]-7-oxo-4-thia-1-azabicyclo[3.2.0]-heptane-2-carboxylic acid hydrochloride (0.54 g, 1.1 mM) in water (35 ml) and 0.7 g, 10% by weight of palladium on 90% by weight carbon was hydrogenated (1 atm.) for 1.5 hrs. After the reaction, the catalyst was removed by filtration and the filtrate was purified on Sephadex LH 20 to give 0.14 g (28% yield) of [2S-(2alpha,5alpha,6beta)]-6-[[[4-[(2-amino-1H-imidazol-1-yl)methyl]-1-piperidinyl]methylene]-amino]-3,3-dimethyl-7-oxo-4-thia-1-azabicyclo[3.2.0]-heptane-2-carboxylic acid hydrochloride.

EXAMPLE 7

(4-(2-cyanoethyl)-1-piperidinecarboxaldehyde 4-(2-Bromoethyl)-1-piperidinecarboxaldehyde (47 g, 0.213M) and NaCN (24 g) in ethanol (470 ml) was refluxed for 4 hours. Solvent was removed, added water (30 ml) and extracted with methylene chloride (4×200 ml). The extracts, dried over NaSO$_4$, were stripped to dryness and then purified on silica gel columns eluted with ethyl acetate to give 4-(2-cyanoethyl-1-pileridinecarboxaldehyde (16 g, 50% yield).

EXAMPLE 8

4-[2-(4,5-Dihydro-1H-imidazol-2-yl)ethyl]piperidine

A mixture containing 4-(2-cyanoethyl)-1-piperidinecarboxaldehyde (10 g, 0.06M) and ethylenediamine p-toluenesulfonate (30 g, 0.129M) were heated at 200° C. for 4½ hours. Crystallization of the crude reaction mixture from isopropanol (70 ml) yielded the desired product as the di-p-toluenesulfonate salt (14 g). The salt was then basified with 2 equivalents of MeONa and distilled (0.2 mmHg, 170° C.) to give 4-[2-(4,5-dihydro-1H-imidazol-2-yl)ethyl]piperidine (4.1 g, 37% yield).

EXAMPLE 9

[2S-(2-alpha,5alpha,6beta)]-6-[[[4-[4,5-Dihydro-1H-imidazol-2-yl)ethyl]-1-piperidinyl]methylene]amino]-3,3-dimethyl-7-oxo-4-thia-1-azabicyclo[3.2.0]heptane-2-carboxylic acid hydrochloride A mixture containing 4-[2-(4,5-dihydro-1H-imidazol-2-yl)ethyl]piperidine (1 g, 0.0055M), methanol (10 ml) and dimethylformamide dimethylacetal (10 ml) was heated at 90° C. for 8 hours. The excess of dimethylformamide was removed in vacuo to give 4-[2-(4,5-dihydro-1H-imidazol-2-yl)ethyl]-1-piperidine carboxaldehyde dimethylacetal. To the mixture of 6-aminopenicillanic acid (1.01 g, 0.0045M) and diisopropylethylamine (0.54 ml) in dried chloroform (30 ml) was added the chloroform solution (20 ml) of the above piperidinecarboxaldehyde dimethylacetal at 0° C. The reaction was stirred at 0° C. for 1 hour and at room temperature for 3 hours. After the reaction, the solvent was removed and the residue dissolved in water (20 ml). The aqueous solution, washed with ethylacetate was acidified to pH3 with dil. HCl and purified on Sephadex LH 20 columns to give [2S-(2alpha,5alpha,6beta)]-6-[[[4-[2-(4,5-dihydro-1H-imidazol-2-yl)ethyl]-1-piperidinyl]methylene]-amino]-3,3-dimethyl-7-oxo-4-thia-1-azabicyclo[3.2.0]-heptane-2-carboxylic acid hydrochloride (1.11 g, 45% yield).

EXAMPLE 10

4-(A3-Cyanopropyl)-1-piperidinecarboxaldehyde 4-(3-Bromopropyl)-1-piperidinecarboxaldehyde (60 g, 0.256M) and NaCN (25 g) in ethanol (600 ml) was refluxed for 7 hours, Solvent was removed, added water (300–400 ml) and extracted with CH$_2$Cl$_2$ (4×200 ml). The extracts, dried over Na$_2$SO$_4$ was stripped to dryness which was purified on silica gel columns, eluted with ethylacetate-hexane (8:2 parts by volume) to yield 4-(3-cyanopropyl)-1-piperidinecarboxaldehyde (28.4 g, 61% yield).

EXAMPLE 11

4-[3-(4,5-Dihydro-1H-imidazol-2-yl)propyl]piperidine

To 4-(3-cyanopropyl)-1-piperidinecarboxaldehyde (10 g, 0.055M), there was added ethylenediamine p-toluenesulfonate (30 g, 0.129M) and the mixture was heated at 200° C. for 4½ hours. The reaction mixture was dissolved in ethanol (100 ml), basified with MeONa (0.26M), filtered and stripped to dryness. The residue was distilled at 170° C., 0.025 mmHg to give 4-[3-(4,5-dihydro-1H-imidazol-2-yl)propyl]-piperidine (7.86 g, 72% yield).

EXAMPLE 12

[2S-(2alpha,5alpha,6beta)]-6-[[[4-[3-(4,5-Dihydro-1H-imidazol-2-yl)propyl]-1-piperidinyl]methylene]-amino]-3,3-dimethyl-7-oxo-4-thia-1-azabicyclo[3.2.0]heptane-2-carboxylic acid hydrochloride By the procedure of the Example 9, the product [2S-(2alpha,5alpha,6beta)]-6-[[[4-[3-(4,5-dihydro-1H-imidazol-2-yl)propyl]-1-piperidinyl]methylene]amino]-3,3-dimethyl-7-oxo-4-thia-1-azabicyclo[3.2.0]heptane-2-carboxylic acid hydrochloride (0.53 g, 18.5% yield) was obtained from 4-[3-(4,5-dihydro-1H-imidazol-2-yl)propyl]piperidine (1.36 g, 0.007M) and 6-aminopenicillanic acid (1.36 g, 0.0063M).

EXAMPLE 13

4-[3-(2-Ethyl-4-methyl-1H-imidazol-1-yl)propyl]-1-piperidinecarboxaldehyde

2-Ethyl-4-methyl-1H-imidazole (3.3 g, 30 mM) and sodium hydride (50% by weight in mineral oil, 80 mM) in dimethylformamide (20 ml) was heated at 50° C. for ½ hour. The solution of 4-(3-bromopropyl)-1-piperidinecarboxaldehyde (7 g, 30 mM) in dimethylformamide (20 ml) was added at 50° C. and stirred at that temperature for 4 hours. After the reaction, solvent was removed in vacuo and water (100 ml) was added and then extracted with ethyl acetate (2×100 ml). The extracts, dried over Na$_2$SO$_4$, was stripped to dryness and purified on silica gel column, eluted with 2% by volume MeOH, 98% by volume CH$_2$Cl$_2$, to give 4-[3-(2-ethyl-4-methyl-1H-imidazol-1-yl)propyl]-1-piperidinecarboxaldehyde as an oil (4.04 g, 51% yield).

EXAMPLE 14

[2S-(2alpha,5alpha,6beta)]-6-[[[4-[3-(2-ethyl-4-methyl-1H-imidazol-1-yl)propyl]piperidinyl]methylene]amino]-3,3-dimethyl-7-oxo-4-thia-1-azabicyclo[3.2.0]heptane-2-carboxylic acid hydrochloride A mixture containing 4-[3-(2-Ethyl-4-methyl-1H-imidazol-1-yl)propyl]-1-piperidinecarboxaldehyde (2 g, 7.5 mM) in dioxane (20 ml) and 1 NHCl (20 ml) was heated at 100° C. for 6 hours. The solvent was then removed and the residue was basified with 1N NaOH to pH 10 and then extracted with $CH_2Cl_2$ (3×30 ml). The combined extracts, dried over $NO_2SO_4$, were stripped to dryness to give an oil (1.71 g, 7.2 mM) which was then heated with dimethylformamide dimethylacetal (20 ml) at about 110° C. for 10 hours. The excess of dimethylformamide was removed to give 4-[3-(2-ethyl-4-methyl-1H-imidazol-1-yl)propyl]-1-piperidine carboxaldehyde dimethylacetal. This acetal dissolved in chloroform (15 ml) was added, at 0° C., to a mixture of 6-aminopenicillanic acid (1.5 g, 7 mM) and diisopropylethylamine (1.28 ml). The resulting reaction mixture was stirred at 0° C. for 1 hour and at room temperature for 3 hours. After the reaction, the solvent was removed in vacuo and the residue was dissolved in water (40 ml). The aqueous solution, washed with ethylacetate was acidified to pH 3 with dil. HCl and purified on Sephadex columns to give [2S-(2-alpha,5alpha,6beta)]-6-[[[4-[3-(2-ethyl-4-methyl-1H-imidazol-1-yl)propyl]piperidinyl]methylene]amino-3,3-dimethyl-7-oxo-4-thia-1-azabicyclo[3.2.0]heptane-2-carboxylic acid hydrochloride (1.18 g, 34% yield).

EXAMPLE 15

4-[3-(2-Nitro-1H-imidazol-1-yl)propyl]-1-piperidinecarboxaldehyde

The mixture of 2-nitroimidazole (11.3 g, 0.1M) and 50% by weight NaH in mineral oil (4.8 g, 0.1M) in dimethylformamide (50 ml) was stirred at room temperature for ½ hr. The solution of 4(3-bromo-propyl)-1-piperidine carboxaldehyde (23.4, 0.1M) in dimethylformamide (20 ml) was added to the above mixture and heated at 110° C. for 15 min. After the reaction, the solvent was removed in vacuo wand water (100 ml) was added and the mixture was extracted with ethylacetate (72×100 ml). The extracts, dried over $Na_2SO_4$, were concentrated and purified on silica gel columns, eluted with 5% by volume MeOH—95% by volume $CH_2Cl_2$ to give 4-[3-(2-nitro-1H-imidazol-1-yl)propyl]-piperidinecarboxaldehyde (22.8 g).

EXAMPLE 16

[2S-(2alpha,5alpha,6beta)]-6-[[[4-[3-(2-nitro-1H-imidazol-1-yl)propyl]piperidinyl]methylene]amino]-3,3-dimethyl-7-oxo-4-thia-1-azabicyclo[3.2.0]heptane-2-carboxylic acid hydrochloride 0.66 molar hydrate A solution of 4-[3-(2-nitro-1H-imidazol-1-yl)propyl]-1-piperidinecarboxaldehyde (3.25 g, 12.2 mM) in dioxane (90 ml) and 1N HCl (90 ml) was heated at 100° C. for 4 hrs. After the reaction, the solvent was removed in vacuo, and the residue, basified with 1N NaOH to pH 10, was extracted with methylenechloride (3×40 ml). The extracts, dried over $Na_2SO_4$ were stripped to give an oil (2.62 g, 11 mM). Without further purification, the resulting crude product (2.62 g) and dimethyl formamide dimethylacetal (30 ml) was heated at 100° to about 110° C. for 10 hrs. The excess of dimethyl formamide dimethylacetal was removed at reduced pressure to give 4-[3-(2-nitro-1H-imidazol-1-yl)propyl]-1-piperidine carboxaldehyde dimethylacetal. This acetal in dry chloroform (30 ml) was added at 0° C. to a mixture of 6-aminopenicillanic acid (2.07 g, 9.8 mL) and diisopropylethylamine (1.69 ml). This reaction mixture was stirred at 0° C. for 1 hr. and then at room temperature for 3 hrs. After this period, the solvent was removed in vacuo, the residue was dissolved in water (50 ml). The resulting aqueous solution, washed with ethylacetate (2×20 ml), was acidified to pH 3 and purified on Sephadex LH 20 columns to give [2S-(2alpha,5alpha,6beta)]-6-[[[4-[3-(2-nitro-1H-imidazol-1-yl)propyl]piperidinyl]-methylene]amino]-3,3-dimethyl-7-oxo-4-thia-1-azabicyclo[3.2.0]heptane-2-carboxylic acid hydrochloride 0.66 molar hydrate (2.3 g, 4.6 mM, 26% yield).

EXAMPLE 17

[2S-(2alpha,5alpha,6beta)]-6-[[[4-[3-(2-Amino-1H-imidazol-1-yl)propyl]piperidinyl]methylene]amino]-3,3-dimethyl-7-oxo-4-thia-1-azabicyclo[3.2.0]heptane-2-carboxylic acid hydrochloride The solution of [2S-(2alpha,5alpha,6beta)]-6-[[[4-[3-(2-nitro-1H-imidazol-1-yl)propyl]piperidinyl]methylene]amino]-3,3-dimethyl-7-oxo-4-thia-1-azabicyclo[3.2.0]heptane-2-carboxylic acid hydrochloride 0.66 molar hydrate (2.86 g, 5.7 mM) in water (250 ml) and 4.2 g of 10% by weight palladium on 90% by weight charcoal was hydrogenated (1 atmosphere pressure) for 1.5 hrs. After the reaction, the catalyst was removed by filtration and the filtrate was freeze-dried to give 1.9 g (4.0 mM, 70% yield) of [2S-(2alpha,5alpha,6beta)]-6-[[[4-[3-(2-amino-1H-imidazol-1-yl)propyl]-piperidinyl]methylene]amino]-3,3-dimethyl-7-oxo-4-thia-1-azabicyclo[3.2.0]heptane-2-carboxylic acid hydrochloride.

EXAMPLE 18

4-[(4,5-Dihydro-1H-Imidazol-2-yl)methyl]piperidine 2-(4-pyridylmethyl)-imidazoline (3.0 g, 0.018M) and platinum oxide (0.3 g) in ethanol (50 ml) and 2N HCl (20 ml) was hydrogenated at 45 psig for 4 hrs. The catalyst was removed by filtration and the solvent was stripped. Crystallization from ethanol gave 4.05 g of 4-[(4,5-dihydro-1H-imidazol-2-yl)methyl]piperidine as dihydrochloride salt (89% yield).

EXAMPLE 19

[2S-(2alpha,5alpha,6beta)]-6-[[[4-[(4,5-Dihydro-1H-Imidazol-2-yl)methyl]-1-piperidinyl]methylene]amino]-3,3-dimethyl-7-oxo-4-thia-1-azabicyclo[3.2.0]heptane-2-carboxylic acid hydrochloride A mixture containing the dihydrochloride salt of 4-[(4,5-dihydro-1H-imidazol-2-yl)methyl]piperidine (8.5 g, 0.035M) and methanol (160 ml) which contained sodium methoxide (0.071M) was stirred at room temperature for 10 minutes and dimethylformamide dimethyl acetal (170 ml) was added and heated at 90° C. for 6 hrs. The excess of dimethylformamide dimethyl acetal was removed to give 4-[(4,5-dihydro-1H-imidazol-2-yl)methyl]-piperidine carboxaldehyde dimethyl acetal. To the mixture of 6-aminopenicillanic acid (6.3 g, 0.029M) and diisopropylethylamine (5.1 ml) in dried chloroform was added the solution (20 ml $CHCl_3$ and 5 ml MeOH) of the above piperidine carboxaldehyde dimethylacetal at 0° C. The reaction was stirred at 0° C. for 1 hr and at room temperature for 3 hrs. After this period, the solvent was removed in vacuo and dissolved in 150 ml of water. The aqueous solution, washed with ethyl acetate was acidified to pH 3 with dilute hydrochloric acid and purified on Sephadex LH$_{20}$ columns to give [2S-(2alpha,5alpha,6beta)]-6-[[[-4-[(4,5-dihydro-1H-imidazol-2-yl)methyl]-1-piperidinyl]methylene]amino]-3,3-dimethyl-7-oxo-4-thia-1-azabicyclo[3.2.0]heptane-2-carboxylic acid hydrochloride (8.1 g, 62% yield).

EXAMPLE 20

4-(1H-Imidazol-2-yl)pyridine 2-(4-pyridyl)-imidazoline (7.0 g, 0.047M) and barium mangnate (52.5 g) in CH$_2$Cl$_2$ (500 ml) were refluxed with stirring for 24 hrs. The reaction mixture was then filtered through diatomaceous earth, washed with methylene chloride and then ethylacetate. The combined filtrates were concentrated and crystallized from ethylacetate-petroleum ether to give 4-(1H-imidazol-2-yl)pyridine (4.7 g, 67% yield).

EXAMPLE 21

4-(1H-Imidazol-2-yl)piperidine 4-(1H-imidazol-2-yl)pyridine (4 g, 0.0275M) and platinum oxide (0.5 g) in ethanol (50 ml) and 1N HCl (60 ml) was reduced at 45 psig of hydrogen for 4 hrs. The reaction mixture was filtered and the filtrate was concentrated and crystallized from methanolethanol to give the 4-(1H-imidazol-2-yl)piperidine as dihydrochloride salt (4.47 g, 88% yield, mp 286°–289°).

EXAMPLE 22

[2S-(2alpha,5alpha,6beta)]-6-[[[4-(1H-Imidazol-2-yl)-1-piperidinyl]methylene]amino]-3,3-dimethyl-7-oxo-4-thia-1-azabicyclo[3.2.0]heptane-2-carboxylic acid hydrochloride trihydrate A solution of the dihydrochloride salt of 4-(1H-imidazol-2-yl)piperidine (0.448 g, 0.002M) in methanol (15 ml) which contained sodium methoxide (0.004M) was stirred at room temperature for about 5 minutes and dimethylformamide dimethyl acetal (10 ml) was added and the mixture was heated at 80° C. for 8 hrs. The excess of dimethylformamide dimethylacetal was removed to give 4-(1H-imidazol-2-yl)-1-piperidine carboxaldehyde dimethylacetal. This acetal was then dissolved in 6 ml of chloroform. To a mixture of 6-aminopenicillanic acid (0.388 g, 0.0018M) and diisopropylethylamine (0.2 ml) in CHCl$_3$ (20 ml) was added the chloroform solution of the above piperidine carboxaldehyde dimethyl acetal at 0° C. The reaction was stirred at 0° C. for 1 hr and room temperature for 3 hrs. After this period, the solvent was removed and the residue dissolved in water (15 ml). The aqueous solution, washed with ethylacetate, was acidified to pH 3 with dil. HCl and purified on Sephadex LH 20 to give [2S-(2alpha,5alpha,6beta)]-6-[[[4-(1H-imidazol-2-yl)-1-piperidinyl]methylene]amino]-3,3-dimethyl-7-oxo-4-thia-1-azabicyclo[3.2.0]heptane-2-carboxylic acid hydrochloride trihydrate (0.245 g, 26% yield).

EXAMPLE 23

4-(4,5-Dihydro-1H-Imidazol-2-yl)Piperidine 4-(4,5-dihydro-1H-imidazol-2-yl)pyridine (2.4 g, 0.016M) and platinum oxide (0.3 g) in ethanol (36 ml) and 1N HCl (35 ml) were reduced at 45 psig of hydrogen for 3½ hrs. The reaction was filtered and the filtrate was concentrated and crystallized from ethanol-acetone (4:6 parts by volume) to give the 4-(4,5-dihydro-1H-imidazol-2-yl)piperidine as dihydrochloride salt (1.7 g, 44%, mp 119°).

EXAMPLE 24

[2S-(2alpha,5alpha,6beta)]-6-[[[4-(4,5-dihydro-1H-imidazol-2-yl)-1-piperidinyl]methylene]amino]-3,3-dimethyl-7-oxo-4-thia-1-azabicyclo[3.2.0]heptane-2-carboxylic acid hydrochloride A solution of the dihydrochloride salt of 4-(4,5-dihydro-1H-imidazol-2-yl)piperidine (0.99 g, 0.0044M) in methanol (10 ml) which contained sodium methoxide (0.009M) was stirred at room temperature for 10 minutes and dimethylformamide dimethylacetal (10 ml) was added and refluxed at 80° C. for 8 hrs. The excess of dimethylformamide dimethylacetal was removed to give 4-(4,5-dihydro-1H-imidazol-2-yl)-1-piperidinecarboxaldehyde dimethylacetal. To a mixture of 6-aminopenicillanic acid (0.785 g, 0.0035M) and diisopropyl ethylamine (0.412 ml) in dry chloroform was added the chloroform solution (30 ml) of the above piperidine-carboxaldehyde dimethyl acetal at 0° C. The reaction was stirred at 0° C. for 1 hr and at room temperature for 3 hrs. After this period, the solvent was removed in vacuo and the residue was dissolved in water (40 ml). The aqueous solution washed with ethylacetate was acidified to pH 3 with dil HCl and purified on Sephadex LH 20 columns to give [2S-(2alpha,5alpha,6beta)]-6-[[[4-(4,5-dihydro-1H-imidazol-2yl)-1-piperidinyl]methylene]amino]-3,3-dimethyl-7-oxo-4-thia-1-azabicyclo[3.2.0]heptane-2-carboxylic acid hydrochloride (0.21 g, 11.5% yield).

EXAMPLE 25

4(2-Cyanoethyl)pyridine

A mixture of 3-(4-pyridyl)-propionamide (7.1 g, 0.47M) in PO Cl$_3$ (25 ml) was heated at about 100° to about 110° C. for 2 hrs. The excess of PO Cl$_3$ was removed in vacuo from the reaction. Thereafter water was added and the resulting solution was basified with aqueous Na$_2$CO$_3$ sol. and extracted with CHCl$_3$. The combined extracts were dried over Na$_2$SO$_4$ and concentrated and distilled at 1 mmHg/118°-120° C. to give 4(2-cyanoethyl)pyridine as an oil (4.8 g, 77% yield).

EXAMPLE 26

4,5,6,7-Tetrahydro-2[2-(4-pyridyl)ethyl]-1H-1,3-diazepine

The mixture of 4-[2-cyanoethyl]pyridine (1.32 g, 0.01M), 1,4-diaminobutane (0.88 g, 0.01M) and 1,4-diaminobutane di-p-toluenesulfonate (4.32 g, 0.01M) was heated at about 190° to about 200° C. for 4 hrs. The residue was stirred with ethanol (20 ml) which contained EtONa (0.02M) and filtered. The filtrate was concentrated and distilled at 0.07 mmHg and a temperature of about 180° to about 200° C. to give 4,5,6,7-tetrahydro-2[2-(4-pyridyl)ethyl]-1H-1,3-diazepine (1.9 g, 93% yield).

EXAMPLE 27

4-[2-(4,5,6,7-Tetrahydro-1H-1,3-diazepin-2-yl)ethyl]-piperidine

The 4,5,6,7-tetrahydro-2[2-(4-pyridyl)ethyl]-1H-1,3-diazepine (1.9 g, 0.009M) and PtO$_2$ (0.25 g) in ethanol (20 ml) and 2 NHCl (15 ml) was reduced at 45 psig of hydrogen. After the hydrogenation, the solvent was removed and the residue was crystallized from ethanol-ether to give 1.5 g of 4-[2-(4,5,6,7-tetrahydro-1H-1,3-diazepin-2-yl)ethyl]piperidine (60% yield) as dihydrochloride salt.

EXAMPLE 28

[2S-(2alpha,5alpha,6beta)]-6-[[[4-[2-(4,5,6,7-tetrahydro-1H-1,3-diazepin-2-yl)ethyl]-1-piperidinyl]methylene]amino]-3,3-dimethyl-7-oxo-4-thia-1-azabicyclo[3.2.0]heptane-2-carboxylic acid hydrochloride The dihydrochloride salt of 4-[2-(4,5,6,7-tetrahydro-1H-1,3-diazepin-S2-yl)ethyl]-piperidine (1.6 g, 5.8 mM) in methanol (12 ml) which contained MeONa (12 mM) and dimethylformamide dimethyl acetal (20 ml) was heated at 90° C. for 8 hrs. The excess of dimethylformamide dimethylacetal was removed in vacuo to give the 4-[2-(4,5,6,7-tetrahydro-1H-1,3-diazepin-2-yl)ethyl] 1-piperidinecarboxaldehyde dimethylacetal. To the mixture of 6-aminopenicillanic acid (1.1 g, 5 mM) and diisopropylethylamine (0.96 ml) in 20 ml dry CHCl₃ was added the solution (CHCl₃ 8 ml: MeOH 1 ml) of the above piperidine-carboxaldehyde dimetylacetal at 0° C. The reaction was stirred at 0° C. for 1 hr and then at room temperature for 3 hrs. The solvent was then removed, and water added (30 ml). The aqueous solution, washed with ethylacetate, was acidified to pH 3 with dilute aqueous HCl and purified on Sephadex LH 20 column to yield [2S-(2alpha,5alpha,6beta)]-6-[[[4-[2-(4,5,6,7-tetrahydro-1H-1,3-diazepin-2-yl)ethyl]-1-piperidinyl]methylene]amino]-3,3-dimethyl-7-oxo-4-thia-1-azabocyclo[3.2.0]heptane-2-carboxylic acid hydrochloride (0.85 g, 38% yield)

EXAMPLE 29

3-(1H-Imidazol-2-yl)pyridine 2-(3-pyridyl)imidazoline (7.2 g, 0.049M), and barium manganate (52.5 g) in CH₂Cl₂ (500 ml) were refluxed for 24 hrs. The reaction mixture was then filtered through diatomaceous earth, washed with ethylacetate (3×200 ml) and methanol (3×100 ml). The combined filtrates were concentrated to yield an oil which was purified on silica gel column, eluted with 20% by volume methanol 80% by volume methylene dichloride, to give 3-(1H-imidazol-2-yl)pyridine (4.66 g, 64.7%).

EXAMPLE 30

3-(1H-Imidazol-2-yl)piperidine 3-(1H-imidazol-2-yl)pyridine (4.0 g, 0.0275M) and platinum oxide (0.5 g) in ethyl alcohol (50 ml) and 1 NHCl (50 ml) was reduced at 45 psig of hydrogen for 4 hrs. The reaction mixture was filtered and the filtrate was stripped to dryness and crystallized from MeOH-EtOH to give 3-(1H-imidazol-2-yl)piperidine (4.5 g, 74% yield, mp 295° dec.).

EXAMPLE 31

[2S-(2alpha,5alpha,6beta)]-6-[[[3-(1H-Imidazol-2-yl)-1-piperidinyl]methylene]amino]-3,3-dimethyl-7-oxo-4-thia-1-azabocyclo[3.2.0]heptane-2-carboxylic acid hydrochloride A mixture containing the dihydrochloride salt of 3-(1H-imidazol-2-yl)piperidine (0.99 g, 0.0044M) and methanol (10 ml) which contained sodium methoxide (0.009M) was stirred at room temperature for 10 min. and dimethylformamide dimethylacetal (10 ml) was added and heated at 90° C. for 8 hrs. The excess of dimethylformamide dimethylacetal was removed to give 3-(1H-imidazol-2-yl)-1-piperidinecarboxaldehyde dimethylacetal. To the mixture of 6-aminopenicillanic acid (0.77 g, 0.0035M) and diisopropyl ethylamine (0.42 ml) in CHCl₃ (30 ml) was added the chloroform solution (30 ml) of the above piperidine carboxaldehyde dimethylacetal at 0° C. The reaction was stirred at 0° C. for 1 hr and then at room temperature for 3 hrs. After this period, the solvent was removed and the residue dissolved in water (30 ml). The aqueous solution, washed with ethylacetate, was acidified to pH 3 with dilute aqueous HCl and purified on Sephadex LH20 columns to give [2S-(2alpha,5alpha,6beta)]-6-[[[3-(1H-imidazol-2-yl)-1-piperidinyl]methylene]amino]-3,3-dimethyl-7-oxo-4-thia-1-azabicyclo[3.2.0]heptane-2-carboxylic acid hydrochloride (0.52 g, 28.8% yield).

EXAMPLE 32

4[3-(1H-Imidazol-1-yl)propyl]-1-piperidinecarboxaldehyde

The mixture of imidazole (0.7 g, 0.01M) and NaH (50% by weight in mineral oil, 0.9 g, 0.018M) in dimethylformamide (60 ml) was heated at 50° C. for ½ hr. and 4-(3-bromopropyl)-1-piperidinecarboxaldehyde (2.93 g, 0.0125M) in dimethylformamide (20 ml) was added. The reaction was heated at 50° C. for 4 hrs. After the reaction, the solvent was removed in vacuo, water was added and the product was extracted with CH₂Cl₂ (3×50 ml). The combined extracts, dried over Na₂SO₄, were stripped to dryness and purified on silica gel column eluted with 10% by volume methanol—90% by volume methylenechloride to give 4[3-(1H-imidazol-1-yl)propyl]-1-piperidinecarboxaldehyde as an oil (2.12 g, 96%).

EXAMPLE 33

4-[3-(1H-Imidazol-1-yl)propyl]-piperidine

A mixture of 4[3-(1H-imidazol-1-yl)propyl]-1-piperidinecarboxaldehyde (2.12 g, 0.0095M) in dioxane (80 ml) and 2NHCl (11 ml) was refluxed for 5½ hrs. After the reaction, the solvent was removed, water was added and the solution was basified with 2N NaOH to pH 10 and extracted with CH₂Cl₂ (3×50 ml). The extracts were concentrated to give an oil (1.55 g, 80%). The dihydrochloride salt of the 4[3-(1H-imidazol-1-yl)propyl]-piperidine which was crystallized from acetone has m.p. 184°-186° C.

EXAMPLE 34

[2S-(2alpha,5alpha,6beta)]-6-[[[4-[3-(1H-Imidazol-1-yl)propyl]-1-piperidinyl]methylene]amino]-3,3-dimethyl-7-oxo-4-thia-1-azabicyclo[3.2.0]heptane-2-carboxylic acid 1.2 mole hydrochloride monohydrate A mixture of 4-[3-(1H-imidazol-1-yl)propyl]-piperidine (1.5 g, 0.0078M) and dimethylformamide dimethylacetal (10 ml) was heated at 100° C. for 16 hrs. The excess of dimethylformamide dimethylacetal was removed to give 4-[3-(1H-imidazol-1-yl)propyl]-1-piperidinecarboxaldehyde dimethylacetal. To the mixture of 6-aminopenicillanic acid (1.16 g, 0.0053M) and diisopropylethylamine (1.03 ml) in dry CHCl₃ (9 ml) was added the above piperidinecarboxaldehyde in CHCl₃ (5 ml) at 0° C. and stirred at that temperature for 1 hr, then at room temperature for 3 hrs. After the reaction, the solvent was removed and the residue dissolved in water (40 ml). The aqueous solution, washed with diethyl ether, was adjusted to pH 3 with dilute aqueous HCl and purified on Sephadex LH 20 column to give [2S-(2alpha,5alpha,6beta)]-6-[[4-[3-(1H-imidazol-1-yl)propyl]-1-piperidinyl]methylene]amino]-3,3-dimethyl-7-oxo-4-thia-1-azabicyclo[3.2.0]heptane-2-carboxylic acid 1.2 mole hydrochloride monohydrate (0.87 g, 39% yield).

EXAMPLE 35

2-(4-Pyridylmethyl)-imidazole

The mixture of 2-(4-pyridylmethyl)-imidazoline (6.6 g, 0.04M) and Raney-Nickle (3 g) was heated initially at 210° C. and gradually raised to 250° C. in 15 min. After the reaction, the reaction was dissolved in ethanol (50 ml) and filtered to remove the catalyst. The filtrate was stripped to dryness and distilled (0.25 mmHg, 180° C.) to give 2-(4-pyridylmethyl)-imidazole (4.1 g, 62% yield).

EXAMPLE 36

4-(1H-Imidazol-2-yl-methyl)-piperidine 2-(4-pyridylmethyl)imidazole (4 g, 0.025M) and platinum oxide (0.4 g) in ethanol (40 ml) and 2NHCl (50 ml) was hydrogenated at 45 psig for 4 hrs. The catalyst was removed by filtration and the filtrate was stripped to dryness. Crystallization from ethanol gave 4-(1H-imidazol-2-yl-methyl)piperidine as the dihydrochloride salt m.p. 251°–252° C. (5.2 g, 87% yield). The mixture of 2-(4-pyridylmethyl)-imidazole (2.38 g, 10 mM) and NaOCH$_3$ (10 mM) in methanol (20 ml) was stirred for 10 min. and filtered. The filtrate was stripped to dryness and distilled from about 180° to about 200° C./0.3 mmHg to give the free base of 4-(1H-imidazol-2-yl-methyl)piperidine.

EXAMPLE 37

[2S-(2alpha,5alpha,6beta)]-6-[[[4-(1H-imidazol-2-yl-methyl)-1-piperidinyl]methylene]amino]-3,3-dimethyl-7-oxo-4-thia-1-azabicyclo[3.2.0]heptane-2-carboxylic acid hydrochloride The free base of 4-(1H-imidazol-2-yl-methyl)piperidine (1.0 g, 0.006M) and dimethylformamide dimethylacetal (15 ml) in methanol (20 ml) were heated at 90° C. for 8 hrs. The excess of dimethylformamide dimethylacetal was removed at the reduced pressure to give 4-(1H-imidazol-2-yl-methyl)piperidine carboxaldehyde dimethylacetal. To the mixture of 6-aminopenicillanic acid (1.16 g, 0.0054M) and diisopropyl ethylamine (0.96 ml) in dry chloroform (20 ml) was added the solution (10 ml CHCl$_3$ and 2 ml MeOH) of the above piperidine carboxaldehyde dimethylacetal at 0° C. The reaction was stirred at 0° C. for 1 hr. and then at room temperature for 3 hrs. After this period, the solvent was removed in vacuo and the residue dissolved in water (20 ml). The aqueous solution, washed with ethylacetate was acidified to pH 3 with dilute aqueous HCl and purified on Sephadex LH 20 columns to give [2S-(2alpha,5alpha,6beta)]-3,3-dimethyl-6-[[[4-(1H-imidazol-2-yl-methyl)-1-piperidinyl]methylene]amino]-3,3-dimethyl-7-oxo-4-thia-1-azabicyclo[3.2.0]heptane-2-carboxylic acid hydrochloride (0.84 g, 33%).

EXAMPLE 38

4-[(2-Triphenylmethylaminomethyl-1H-imidazol-1-yl)methyl]-1-piperidinecarboxaldehyde A mixture of 2-triphenylmethylimidazole (0.34 g, 0.001M) and sodium hydride (0.057 g, 50% by weight in mineral oil, 0.0024M) in dimethylformamide (10 ml) was stirred at room temperature for ½ hr and heated to 50° C. To the above mixture, a solution of 4-bromomethyl-1-piperidinecarboxaldehyde (0.47 g, 0.001M) in dimethylformamide (2 ml) was added and the reaction was continued by maintaining heating at 50° C. for 4 hrs. After the reaction, solvent was removed in vacuo and water (20 ml) was added. The mixture was extracted with ethylacetate and the extracts, dried over sodium sulfate, were stripped to dryness. Purification on preparative thin layer chromatography plates, eluting with 5% by volume of methanol in 95% by volume chloroform gave 4-[(2-triphenylmethylaminomethyl-1H-imidazol-1-yl)methyl]-1-piperidinecarboxaldehyde (0.176 g, 37.6% yield).

EXAMPLE 39

4-[(2-Triphenylmethylaminomethyl-1H-Imidazol-1-yl)methyl]-piperidine

A mixture of 4-[(2-triphenylmethylaminomethyl-1H-imidazol-1-yl)methyl]-1-piperidinecarboxaldehyde (0.48 g, 0.00103M), 2N sodium hydroxide (24 ml) and methanol (24 ml) was heated at 50° C. for 4 hrs. The reaction was concentrated to about 20 ml at room temperature and extracted with ethylacetate. The extracts, dried over sodium sulfate, was stripped to dryness and purified on preparative thin layer chromatography plates to give 4-[(2-triphenylmethylaminomethyl-1H-imidazol-1-yl)methyl]-piperidine (0.167 g, 37% yield).

EXAMPLE 40

[2S-(2alpha,5alpha,6beta)]-6-[[[4-[[2-(Aminomethyl)-1H-imidazol-1-yl]methyl]-1-piperidinyl]methylene]amino]-3,3-dimethyl-7-oxo-4-thia-1-azabicyclo[3.2.0]heptane 2-carboxylic acid hydrochloride A mixture of 4-[(2-triphenylmethylaminomethyl-1H-imidazol-1-yl)methyl]piperidine (1.45 g, 0.0033M) and dimethylformamide dimethylacetal was heated at 100° C. for 8 hrs. After this period, the reaction was stripped to dryness to give 4-[(2-triphenylmethylaminomethyl-1H-imidazol-1-yl)methyl]-piperidine carboxaldehyde dimethylacetal. The solution of the piperidinecarboxaldehydedimethylacetal in methylene chloride (5 ml) was added to the mixture of 6-aminopenicilanic acid (0.57 g, 0.0026M) and diisopropylethylamine (0.45 ml) in methylene chloride (5 ml) at 0° C. and stirred at room temperature for 3 hrs. The solvent was removed and the residue was stirred for 2 hrs in water (20 ml) which was maintained at pH 3 with 1NHCl. The mixture was filtered and the filtrate was purified on Sephadex LH 20 columns to give [2S-(2alpha,5alpha,6beta)]-6-[[[4-[[2-(aminomethyl)-1H-imidazol-1-yl]methyl]-1-piperidinyl]methylene]amino]-3,3-dimethyl-7-oxo-4-thia-1-azabicyclo[3.2.0]heptane-2-carboxylic acid hydrochloride (0.27 g, 24% yield).

EXAMPLE 41

1-[3-(4-Piperidinyl)propyl]-1H-imidazole-2-amine

A mixture of 4[3-(2-carbobenzyloxyamino-1H-imidazol-1-yl)propyl]-1-piperidinecarboxaldehyde (2.3 g, 0.0062M) in dioxane (360 ml) and 0.5 NHCl (25 ml) was heated to reflux for 5 hrs. After the reaction, the solvent was removed and crystallized in ethanol to give 1-[3-(4-piperidinyl)propyl]-1H-imidazole-2-amine as the dihydrochloride salt mp 220-1° C. (1.075 g, 82% yield). This dihydrochloride salt (1.075 g) was converted to the free base (0.5 g, 39% yield) by passing through basic ion-exchange resin (AGT-1-X4) and eluted with water.

EXAMPLE 42

[2S-(2alpha,5alpha,6beta)]-6-[[[-4-[3-]2-[[(dimethylamino)methylene]amino]-1H-imidazol-1-yl]propyl]-1-piperidinyl]methylene]amino]-3,3-dimethyl-7-oxo-4-thia-1-azabicyclo[3.2.0]heptane-2-carboxylic acid 1.7 molar hydrochloride 2.6 molar hydrate A mixture of 1-[3(4-piperidinyl)propyl]-1H-imidazole-2-amine (0.5 g, 0.0024M) and dimethylformamide dimethylacetal (7 ml) was heated at 100° C. for 10 hrs. The reaction was then stripped to dryness to give 4-[3-(2[[[dimethylamino)methylene]amino]-1H-imidazol-1-yl]propyl]-1-piperidinecarboxaldehyde dimethylacetal. The solution of the piperidinecarboxaldehyde dimethylacetal in chloroform (4 ml) was added to the mixture of 6-aminopenicillanic acid (0.46 g, 0.0216M) and diisopropylethylamine (0.37 ml) in chloroform (10 ml) at 0° C. and then stirred at room temperature for 3½ hrs. After this period, the solvent was removed and water (20 ml) was added. The aqueous solution, after being washed with ethylacetate, was acidified from about pH 3 to about 3.5 and purified on Sephadex L-20 columns to give [2S-(2alpha,5alpha,6beta)]-6-[[[4--[3-[2-[[(dimethylamino)methylene]amino]-1H-imidazol-1-yl]propyl]-1-piperidinyl]-methylene]amino]-3,3-dimethyl-7-oxo-4-thia-1-azabicyclo[3.2.0]heptane-2-carboxylic acid 1.7 molar hydrochloride 2.6 molar hydrate (0.64 g, 64% yield).

EXAMPLE 43

4-[2-(1-Ethyl-4,5-dihydro-imidazol-2-yl)ethyl]-pyridine

A mixture of 4-(2-cyanoethyl)pyridine (1.32 g, 0.01M) and N-ethyl-1,2-diaminoethane mono-p-toluenesulfonate (5.5 g, 0.02M) were heated at 190° C. for 4 hrs under nitrogen. The reaction mixture was dissolved in ethanol (30 ml) and sodium ethoxide (0.02M) in ethanol (50 ml) was added. The mixture was filtered and the filtrate was stripped to dryness and distilled at 130° C./0.2 mmHg to yield 4-[2-(1-ethyl-4,5-dihydro-imidazol-2-yl)ethyl]-pyridine (1.2 g, 60% yield).

EXAMPLE 44

4-[2-(1-Ethyl-4,5-dihydro-imidazol-2-yl)ethyl]piperidine

The solution of 4-[2-(1-ethyl-4,5-dihydro-imidazol-2-yl)ethyl]-pyridine (1.1 g, 0.0054M) in ethanol (15 ml) and water (15 ml) was added con.HCl (3 ml) and platinum oxide (0.2 g). The mixture was hydrogenated at 45 psig for 4 hrs. The catalyst was removed by filtration and the filtrate was stripped to dryness in vacuo. The residue was dissolved in methanol (25 ml) and sodium methoxide (0.011M) was added and filtered. The filtrate was stripped to dryness and distilled at about 150° to about 175° C./0.2 mmHg to yield 4-[2-(1-ethyl-4,5-dihydro-imidazol-2-yl)ethyl]piperidine as an oil (0.8 g, 70% yield).

EXAMPLE 45

[2S-(2alpha,5alpha,6beta)]-6-[[[4-[2-(1-ethyl-4,5-dihydro-1H-imidazol-2-yl)ethyl]-1-piperidinyl]methylene]amino]-3,3-dimethyl-7-oxo-4-thia-1-azabicyclo[3.2.0]heptane-2-carboxylic acid hydrochloride A solution of 4-[2-(1-ethyl-4,5-dihydro-imidazol-2-yl)ethyl]piperidine (0.66 g, 0.0031M) in methanol (6 ml) and dimethylformamide dimethylacetal (6 ml) was heated at 90° C. for 6 hrs. Removal of the excess of dimethylformamide dimethylacetal gave 4-[2-(1-ethyl-4,5-dihydro-imidazol-2-yl)ethyl]-1-piperidine carboxaldehyde dimethylacetal. The solution of the piperidine carboxaldehyde dimethylacetal in chloroform (5 ml) was then added to a mixture of 6-aminopenicillanic acid (0.6 g, 0.0028M) and diisopropylethylamine (0.5 ml) in chloroform (6 ml) at 0° C. The reaction was stirred at 0° C. for 1 hr and room temperature for 3 hrs. The solvent was removed and water (10 ml) was added. After being washed with ethylacetate, the aqueous solution, acidified from about pH 3 to about 3.5 was purified on Sephadex LH 20 columns to give [2S-(2alpha,5alpha,6beta)]-6-[[[4-[2-(1-ethyl-4,5-dihydro-1H-imidazol-2-yl)ethyl]-1-piperidinyl]methylene]amino]-3,3-dimethyl-7-oxo-4-thia-1-azabicyclo[3.2.0]heptane-2-carboxylic acid hydrochloride (0.46 g, 35% yield).

EXAMPLE 46

1,4,5,6-Tetrahydro-2-[(4-piperidinyl)methyl]-pyrimidine

A mixture of 4-cyanomethyl piperidine-1-carboxaldehyde (4. g, 0.026M) and 1,3-diaminopropane mono p-toluenesulfonate (7.3 g, 0.052M) was heated at 100° C. for ½ hrs and 200° C. for 2 hrs. The reaction mixture was dissolved in ethanol (50 ml) and sodium ethoxide (0.052M) was added. The mixture was filtered and the filtrate was stripped to dryness and distilled from about 170° to about 190° C./0.2 mmHg to yield 1,4,5,6-tetrahydro-2-[(4-piperidinyl)methyl]-pyrimidine (2.7 g, 56.7% yield). This compound was characterized as dihydrochloride salt, mp 279°-28° C.(EtOH).

EXAMPLE 47

[2S-(2alpha,5alpha,6beta)]-6-[[[4-[(1,4,5,6-tetrahydro-2-pyrimidinyl)methyl]-1-piperidinyl]methylene]amino]-3,3-dimethyl-7-oxo-4-thia-1-azabicyclo[3.2.0]heptane-2-carboxylic acid hydrochloride A solution of 1,4,5,6-tetrahydro-2-[(4-piperidinyl)methyl]-pyrimidine (0.9 g, 0.005M) in methanol (5 ml) and dimethylformamidedimethylacetal (15 ml) was heated at 90° C. for 8 hrs. The reaction was then stripped to dryness to yield 4-[(1,4,5,6-tetrahydro-2-pyrimidyl)methyl]-1-piperidinecarboxaldehyde dimethylacetal. The solution of the piperidine carboxaldehyde dimethylacetal in methylene chloride (5 ml) was added to a mixture of 6-aminopenicillanic acid (0.97 g, 0.0045M) and diisopropylethylamine (0.76 ml) in methylene chloride (10 ml) at 0° C. The reaction was stirred at 0° C. for 1 hr and room temperature for 3 hrs. The solvent was removed and water (20 ml) was added. After being washed with ethyl acetate, the aqueous solution, acidified to pH 3 to about 3.5, was purified on Sephadex LH 20 columns to give [2S-(2alpha,5alpha,6beta)]-6-[[[4-[(1,4,5,6-tetrahydro-2-pyrimidinyl)methyl]-1-piperidinyl]methylene]amino]-3,3-dimethyl-7oxo-4-thia-1-azabicyclo[3.2.0]heptane-2-carboxylic acid hydrochloride (0.14 g, 7% yield).

EXAMPLE 48

1-[3-(4-Piperidinyl)propyl]-1H-imidazole-2-carboxylic acid 1.75 molar hydrochloride 0.65 molar hydrate The solution of 4-[3-(2-hydroxymethyl-1H-imidazol-1-yl)propyl]-1-piperidine carboxaldehyde in acetone (63 ml) was cooled to 0° C. and potassium permanganate (5.5 g, 0.035M) was added portionwise. After complete addition, the reaction was stirred at 0° C. for 2 hrs. The acetone solution was separated by filtration, and the residue was stirred twice with water (50 ml). The aqueous solution was freeze dried to yield 4-[3-(2-carboxy-1H-imidazol-1-yl)propyl]-1-piperidine carboxaldehyde (5.5 g, 83% yield). This product (7.1 g, 0.027M) in water (26 ml) and 1N NaOH (26 ml) was heated at 100° C. for 5 hrs. The reaction was adjusted pH 6 and purified on ion-exchange column (Bio-Rex 70) eluted with 0.01N, 0.02N, 0.04N, 0.08N and 0.1N HCl solution successively to give 1-[3-(4-piperidinyl)propyl]-1H-imidazole-2-carboxylic acid 1.75 molar hydrochloride 0.65 molar hydrate (4.6 g, 73% yield).

EXAMPLE 49

[2S-(2alpha,5alpha,6beta)]-6-[[[1-[(3-(2-carboxy-1H-imidazol-1-yl)propyl]-1-piperidinyl]methylene]amino]-3,3-dimethyl-7-oxo-4-thia-1-azabicyclo[3.2.0]heptane-2-carboxylic acid hydrate A mixture of 1-[3-(4-piperidinyl)propyl]-1H-imidazole-2-carboxylic acid 1.75 molar hydrochloride 0.65 molar hydrate (1.3 g, 0.0047M) and sodium methoxide (0.005M) in methanol (23 ml) was added to dimethylformamide dimethylacetal (15 ml) and heated at 80° C. for 8 hrs. The reaction mixture was filtered and stripped to dryness to give 4-[3-(2-carboxy-1H-imidazol-1-yl)propyl]-1-piperidine carboxaldehyde. The solution of the above piperidine carboxaldehyde dimethylacetal in methanol (5 ml) was then added to a mixture of 6-aminopenicillanic acid (0.81 g, 0.0037M) and diisopropylethylamine (0.4 ml) in chloroform (30 ml) at 0° C. The reaction was stirred at 0° C. 2 hrs and room temperature for 2 hrs. The solvent was removed and water (15 ml) was added. After being washed with ether, the aqueous solution, acidified to pH 3 to about 3.5, was purified on Sephadex LH 20 columns to give [2S-(2alpha,5alpha,6beta)]-6-[[[1-[(3-(2-carboxy-1H-imidazol-1-yl)propyl]-1-piperidinyl]methylene]amino]-3,3-dimethyl-7-oxo-4-thia-1-azabicyclo[3.2.0]heptane-2-carboxylic acid hydrate (0.38 g, 17% yield).

EXAMPLE 50

4-[3-(1H-2-Hydroxymethyl-imidazol-1-yl)propyl]-1-piperidine-carboxaldehyde

4-[3(1H-imidazol-1-yl)propyl)]-1-piperidinecarboxaldehyde (22 g, 0.1M) and 37% by weight aqueous formaldehyde (25.4 g) were heated at 140° C. in autoclave for 5 hrs. After the reaction, the solvent was removed and the residue purified on silica gel, eluted with 5% by volume MeOH-CHCl₃ 95% by volume then 10% by volume MeOH-90% by volume CHCl₃ to give 4-[3-(1H-2-hydroxymethyl-imidazol-1-yl)propyl]-1-piperidine carboxaldehyde (10 g, 40% yield).

EXAMPLE 51

4-[3-(1H-3-Hydroxymethyl-imidazol-1-yl)propyl]-piperidine

A mixture of 4-[3-(1H-2-hydroxymethyl-imidazol-1-yl)propyl]-1-piperidinecarboxaldehyde (1.5 g, 0.0059M) in dioxane (45 ml) and 0.5N HCl (45 ml) were heated and refluxed for 4 hrs. After the reaction, the mixture was stripped to dryness to yield 1.5 g of 4-[3(1H-2-hydroxymethyl-imidazol-1-yl)propyl]piperidine as HCl salt (m.p. 180°–184°, 98% by weight yield). The HCl salt of 4-[3-(1H-2-hydroxymethylimidazol-1-yl)propyl]-piperidine was passed through a basic ion-exchange resin (AG-1-4X) to give 4-[3-(1H-2-hydroxymethyl-imidazol-1-yl)propyl]piperidine as free base (1.4 g).

EXAMPLE 52

[2S-(2alpha,5alpha,6beta)]-6-[[[4-[3-[2-(hydroxymethyl)-1H-imidazol-1-yl]propyl]-1-piperidinyl]methylene]amino]-3,3-dimethyl-7-oxo-4-thia-1-azabicyclo[4.2.0]heptane-2-carboxylic acid hydrochloride 1.1 molar hydrate A mixture of 4-[3-(1H-2-hydroxymethyl-imidazol-1-yl)propyl]piperidine (0.3 g, 0.0013M) and dimethylformamide dimethylacetal (10 ml) was heated at 80° C. for 8 hrs. After the reaction, the mixture was stripped to dryness and methanol (2 ml) was added and heated for 10 min. at 100° C. The solvent was removed in vacuo to give 4-[3-(1H-2-hydroxymethyl-imidazol-1-yl)propyl]-1-piperidinecarboxaldehyde dimethylacetal. The solution of the above piperidine carboxaldehyde dimethylacetal in chloroform (5 ml) was then added to a mixture of 6-aminopenicillanic acid (0.289 g, 0.0013M) and diisopropylethylamine (0.24 ml) in chloroform (10 ml) at 0° C. The reaction was stirred at 0° C. for 1 hr and room temperature for 3 hrs. The solvent was removed and water (10 ml) was added. After being washed with diethyl ether, the aqueous solution, acidified to a pH 3 to about 3.5 was purified on Sephadex LH 20 columns to give [2S-(2alpha,5alpha,6beta)]-6-[[[4-[3-[2-hydroxymethyl)-1H-imidazol-1-yl]propyl]-1-piperidinyl]methylene]amino]-3,3-dimethyl-7-oxo-4-thia-1-azabicyclo[4.2.0]heptane-2-carboxylic acid hydrochloride 1.1 molar hydrate (0.094 g, 14% yield).

EXAMPLE 53

4-[3-(2,4,5-Trimethyl-1H-imidazol-1-yl)propyl]-1-piperidine carboxaldehyde

A mixture of trimethyloxazole (10.18 g, 0.091M), 4[3-aminopropyl]-1-piperidinecarboxaldehyde and acetic acid (0.16 g) were heated at 145° C. for 6 hrs. After the reaction, the excess of trimethyl oxazole was removed at reduced pressure and the residue was purified on silica gel column eluted with 4 to 10% of methanol by volume in CHCl₃ to yield 4-[3-(2,4,5-trimethyl-1H-imidazol-1-yl)propyl]-1-piperidinecarboxaldehyde as an oil (3.3 g, 50% yield).

EXAMPLE 54

4-[3-(2,4,5-Trimethyl-1H-imidazol-1-yl)propyl]-1-piperidine

A solution of 4-[3-(2,4,5-trimethyl-1H-imidazol-1-yl)propyl]-1-piperidinecarboxaldehyde (0.84 g, 0.0032M) in 1N HCl (20 ml) and dioxane (20 ml) was heated at 100° C. for 4 hrs. After the reaction, the solvent was removed and to the residue there was added 1N NaOH (20 ml). The resulting mixture was extracted with chloroform (30 ml×3). The combined extract, dried over sodium sulfate, were stripped to dryness to yield 4-[3-(2,4,5,-trimethyl-1H-imidazol-1-yl)propyl]-1-piperidine (0.75 g).

EXAMPLE 55

[2S-(2alpha,5alpha,6beta)]-6[[4-[3-[(2,4,5-trimethyl-1H-imidazol-1-yl)propyl]-1-piperidinyl]methylene]amino]-3,3-dimethyl-7-oxo-4-thia-1-azabicyclo[3.2.0]heptane-2-carboxylic acid hydrate hydrochloride A mixture of 4-[3-(2,4,5-trimethyl-1H-imidazol-1-yl)propyl]-1-piperidine (0.75 g, 0.0032M) and dimethylformamide dimethylacetal (20 ml) was heated at 100° C. for 9 hrs. The reaction was stripped to dryness to yield 4-[3-(2,4,5-trimethyl-1H-imidazol-1-yl)propyl]-1-piperidinecarboxaldehyde dimethylacetal. The solution of the above piperidine carboxaldehyde dimethylacetal in chloroform (4 ml) was then added to a mixture of 6-aminopenicillanic acid (0.67 g, 0.003M) and diisopropylethylamine (0.47 ml) in chloroform (12 ml) at 0° C. The reaction was stirred at 0° C. for 1 hr and room temperature for 3 hrs. Solvent was removed and water (15 ml) was added. After being washed with diethyl ether, the aqueous solution, acidified to a pH 3 to about 3.5, was purified on Sephadex LH 20 columns to give [2S-(2alpha,5-alpha,6beta)]-6[[4-[3-[(2,4,5-trimethyl-1H-imidazol-1-yl)propyl]-1-piperidinyl]methylene]amino]-3,3-dimethyl-7-oxo-4-thia-1-azabicyclo[3.2.0]heptane-2-carboxylic acid hydrate hydrochloride (0.71 g, 46% yield).

EXAMPLE 56

4-(Bromomethyl)-1-piperidinecarboxaldehyde

A one-liter, three-necked flask equipped with a mechanical stirrer, dropping funnel, and nitrogen bubbler was charged with 20 g (0.155 mol) of isonipecotic acid and 140 mL of tetrahydrofuran. The flask was cooled in an ice bath and 233 mL of (1M) diborane/THF was added dropwise. The bath was removed, the reaction sitrred two hours at room temperature and then heated for six hours in an 80° bath. The flask was cooled in an ice bath and 140 mL of methyl alcohol added dropwise. The resulting solution was stripped to dryness and 200 mL of absolute alcohol was added followed by slow addition of 50 mL of 10% by weight of anhydrous HCl in absolute alcohol. This alcoholic solution was heated 2½-3 hours at reflux. The reaction was then stripped to dryness and traces of water removed by azeotropic distillation with benzene on the rotary evaporator. The azeotroping procedure was repeated followed by drying in vacuo at room temperature. The crude hydrochloride was used in the next step.

The flask containing the above material was equipped with a mechanical stirrer, dropping funnel, condenser, and nitrogen bubbler, placed in a 55° bath and 25 mL of phosphorous tribromide was added dropwise. Then HBr fumes came through the bubbler, the bath was removed and addition was continued. The heating was continued after addition and continued at 100° for 90 minutes. The reaction was cooled to 25° and anhydrous ether added to convert the reaction product into a granular solid with vigorous stirring. The solid was filtered under nitrogen to give 45.6 g of crude hydrobromide salt.

A two liter, three-necked flask equipped with a mechanical stirrer, dropping funnel, nitrogen bubbler and thermometer was charged with 45.6 g of 4-(bromomethyl)piperidine hydrobromide, 300 mL of tetrahydrofuran and 300 mL of dimethylformamide and cooled to 0°. To the cooled solution was added 27.2 mL of acetic formic anhydride below 5°. When the addition was completed, 54.4 mL of triethylamine was added dropwise between 0° and 5°. The cooling bath was removed and the reaction stirred overnight at room temperature. The salts were removed by filtration and the solvent removed in vacuo to yield a yellow oil. The oil was treated with 100 mL of brine and then extracted with three 100 mL portions of diethyl ether. The ether was dried over anhydrous sodium sulfate. Removal of the ether afforded 24.6 g of light yellow oil. The crude oil was purified by high pressure liquid chromatography using two columns. Removal of the solvent from the desired fractions gave 18.0 g (56.7% yield) of 4-(bromomethyl)-1-piperidinecarboxaldehyde.

EXAMPLE 57

4-[(1H-Imidazol-1-yl)methyl]-piperidine

To a mixture of sodium hydride (5.04 g, 50% by weight in mineral oil, 0.105M) in dimethylformamide (50 ml) was added the solution of imidazole (7.13 g, 0.104M) in dimethylformamide (100 ml) at room temperature and then stirred for additional ½ hr. The reaction was then heated at 50° C. and the solution of 4-(bromomethyl)-1-piperidine carboxaldehyde (18 g, 0.087M) in dimethylformamide (100 ml) was added slowly. After the addition, the reaction mixture heating was continued at 50° C. for 4 hrs. The solvent was removed in vacuo, water (about 200 ml) was added to the residue and the mixture was extracted with methylene chloride. The combined extracts, dried over sodium sulfate, was stripped to dryness to give the crude product (12 g) which was purified on silica gel column eluted with methanol-chloroform (1:9 v/v) to give 7.3 g of 4[1H-imidazol-1-yl)methyl]-1-piperidinecarboxaldehyde. The piperidinecarboxaldehyde (7.3) in 2N HCl (100 ml) and dioxane (100 ml) was heated at 100° C. for 5½ hr. After the reaction, solvent was removed and the residue, dissolved in water (100 ml), was basified with 4N NaOH to pH 11 and extracted with methylene chloride. The combined extracts, dried over sodium sulfate, were stripped to dryness to yield 6.0 g of 4-[(1H-imidazol-1-yl)methyl]-piperidine (40% yield).

EXAMPLE 58

[2S-(2alpha,5alpha,6beta)]-6-[[[4-(1H-Imidazol-1-ylmethyl)-1-piperidinyl]methylene]amino]-3,3-dimethyl-6-oxo-4-thia-1-azabicyclo[3.2.0]heptane-2-carboxylic acid A mixture of 4-[(1H-imidazol-1-yl)methyl]-piperidine (5 g, 0.03M) and dimethylformamide dimethylacetal (40 ml) was heated at 100° C. for 8 hrs. Removal of the excess of dimethylformamide dimethylacetal gave 4-[(imidazol-1-yl)methyl]-1-piperidine carboxaldehyde dimethylacetal (6.33 g) which was dissolved in methylene chloride (25 ml) and added to the mixture of 6-aminopenicillanic acid (5.15 g, 0.024M) and diisopropylethylamine (3.14 ml) in methylene chloride (90 ml) at 0° C. The reaction was stirred at 0° C. for 1 hr and room temperature for 3 hrs. The solvent was then removed and water (80 ml) was added. After being washed with ethylacetate, the aqueous solution, acidified to pH 3, was purified on Sephadex LH 20 columns to give [2S-(2alpha,5alpha,6beta)]-6-[[[4-(1H-imidazol- 1-yl-methyl)-1-piperidinyl]methylene]amino]-3,3-dimethyl-6-oxo-4-thia-1-azabicyclo[3.2.0]heptane-2-carboxylic acid (5.2 g, 55% yield).

EXAMPLE 59

4-[3-(2-methyl-1H-imidazol-1-yl)-propyl]-1-piperidinecarboxaldehyde

A mixture of 2-methylimidazole (2 g, 0.025M) and sodium hydride (1.2 g, 50% in mineral oil, 0.025M) in dimethylformamide (20 ml) was stirred at room temperature for ½ hr. The reaction mixture was then heated at 50° C. and the solution of 4(3-bromopropyl)piperidine carboxaldehyde (4.6 g, 0.02M) in dimethylformamide (20 ml) was added slowly. After completing the addition, the reaction was heated at 50° C. for 4 hrs and then solvent was removed in vacuo. Water (80 ml) was added to the residue and the mixture was extracted with methylene chloride. The combined extracts, dried over sodium sulfate, were stripped to dryness to yield an oil. The oil was purified on silica gel column, eluted with methanol chloroform (1:9 v/v) to give 4-[3-(2-methyl-1H-imidazol-1-yl)-propyl]-1-piperidinecarboxaldehyde (3.86 g, 88% yield).

EXAMPLE 60

4-[3-(2-Methyl-1H-imidazol-1-yl)propyl]piperidine

A mixture of 4-[3-(2-methyl-1H-imidazol-1-yl)propyl]-1-piperidinecarboxaldehyde (3.8 g, 0.016M) in dioxane (100 ml) and 2N HCl (25 ml) was heated and refluxed for 5½ hrs. After this period, solvent was removed, and 1N NaOH (50 ml) was added to the residue. This mixture was then extracted with methylene chloride (5×50 ml). The combined extracts, dried over sodium sulfate, were stripped to dryness to yield 4-[3-(2-methyl-1H-imidazol-1-yl)propyl]piperidine (2.3 g, 65% yield).

EXAMPLE 61

[2S-(2alpha,5alpha,6beta)]-3,3-Dimethyl-6-[[[4-[3-(2-methyl-1H-imidazol-1-yl)propyl]-1-piperidinyl]methylene]amino]-7-oxo-4-thia-1-azabicyclo[3.2.0]heptane-2-carboxylic acid 1.15 molar hydrochloride 1.75 molar hydrate A mixture of 4-[3-(2-methyl-1H-imidazol-1-yl)propyl]piperidine (2.3 g, 0.0105M) and dimethylformamide dimethylacetal (20 ml) was heated at 100° C. for 6 hrs. Removal of the excess of dimethylformamide dimethylacetal gave 4-[3-(2-methyl-1H-imidazol-1-yl)propyl]-1-piperidine carboxaldehyde dimethylacetal. A solution of this piperidine carboxaldehyde dimethylacetal in methylene chloride (10 ml) was added to a mixture of 6-aminopenicillanic acid (2.16, 0.01M) and diisopropyl ethylamine (1.15 ml) in methylene chloride (50 ml) at 0° C. The reaction was stirred at 0° C. for 1 hr and room temperature for 3 hrs. The solvent was removed and water (50 ml) was added. After being washed with ether, the aqueous solution, acidified to pH 3, was purified on Sephadex LH 20 columns to give [2S-(2alpha,5alpha,6beta)]-3,3-dimethyl-6-[[[4-[3-(2-methyl-1H-imidazol-1-yl)propyl]-1-piperidinyl]methylene]amino]-7-oxo-4-thia-1-azabicyclo[3.2.0]heptane-2-carboxylic acid 1.15 molar hydrochloride 1.75 molar hydrate (1.76 g, 33% yield).

EXAMPLE 62

Hexahydro-4-[2-(1H-imidazol-1-yl)ethyl]-1H-azepinecarboxaldehyde

To a mixture of sodium hydride (3.4 g, 50% by weight in mineral oil, 0.071M) in dimethylformamide (50 ml) was added the solution of imidazole (4.8 g, 0.071M) in dimethylformamide (100 ml) and the reaction was stirred at room temperature for ½ hrs then heated to 50° C. To the above reaction mixture, a solution of hexahydro-4-bromo-1H-azepinecarboxaldehyde (13.9 g, 0.059M) in dimethyl formamide (150 ml) was added slowly at 50° C. and continued to stir at that temperature for 2½ hrs the solvent was removed in vacuo, water (300 ml) was added and the mixture was extracted with ethylacetate (4×200 ml). The combined extracts, dried over sodium sulfate, were stripped to dryness and purified on silica gel, eluted with 2% by volume of methanol in methylene chloride to yield hexahydro-4-[2-(1H-imidazol-1-yl)ethyl]-1H-azepinecarboxaldehyde (12 g, 90% yield).

EXAMPLE 63

Hexahydro-4-[2-(1H-imidazol-1-yl)ethyl]-1H-azepine

A mixture of hexahydro-4-[2-(1H-imidazol-1-yl)ethyl]-1H-azepine-carboxaldehyde (11 g, 0.05M) in dioxane (1.65 ml) and 2N HCl (82 ml) was heated and refluxed for 15 hrs. The solvent was removed, water (100 ml) was added and the resulting mixture was washed with methylene chloride (3×20 ml). After washing, the aqueous solution was basified with 4N NaOH to pH 12 and extracted with methylene chloride (4×75 ml). The combined extracts, dried over sodium sulfate, were stripped to yield hexahydro-4-[2-(1H-imidazol-1-yl)ethyl]-1H-azepine as an oil (6 g, 62% yield). This compound was characterized as dihydrochloride salt m.p. 176°–177° C.

EXAMPLE 64

[2S-(2alpha,5alpha,6beta)]-6-[[4-[Hexahydro[2-(1H-imidazol-1-yl)ethyl]-1H-azepin-1-yl]methylene]amino]-3,3-dimethyl-7-oxo-4-thia-1-azabicyclo[3.2.0]heptane-2-carboxylic acid 1.2 molar hydrochloride hydrate (diastereomers)

A mixture of hexahydro-4-[2-(1H-imidazol-1-yl)ethyl]-1H-azepine (6.0 g, 0.031M) and dimethylformamide dimethylacetal (33 ml) was heated at 100° C. for 4 hrs. The reaction was stripped to dryness to give hexahydro-4-[2-(1H-imidazol-1-yl)ethyl]-1H-azepine carboxaldehyde dimethylacetal. The solution of the hexahydroazepine carboxaldehyde dimethylacetal in methylene chloride (40 ml) was added to the mixture of 6-aminopenicillanic acid (5.7 g, 0.026M) and diisopropylethylamine (3.15 ml) in methylene chloride (150 ml) at 0° C. and stirred at 0° C. for 1 hr, room temperature for 3 hrs. The solvent was removed and water (100 ml) was added. After being washed with ether, the aqueous solution, acidified to pH 3, was purified on Sephadex LH 20 columns to give [2S-(2alpha,5alpha,6beta)]-6-[[4-[hexahydro[2-(1H-imidazol-1-yl)ethyl]-1H-azepin-1-yl]methylene]amino]-3,3-dimethyl-7-oxo-4-thia-1-azabicyclo[3.2.0]heptane-2-carboxylic acid 1.2 molar hydrochloride hydrate (diastereomers) (4.0 g, 32% yield).

EXAMPLE 65

4-[(4,5-Dihydro-5,5-dimethyl-1H-imidazol-2-yl)methyl]-piperidine

A mixture containing 4(cyanomethyl)-1-piperidinecarboxaldehyde (3.5 g, 0.023M) and 1,2-diamino-2-methylpropane mono-p-toluenesulfonate (12.4 g, 0.047M) was heated at 185° C. under nitrogen for 5 hrs. The reaction mixture was dissolved in ethanol (20 ml), basified with sodium ethoxide (0.052M), filtered and stripped to dryness. The residue was distilled at 150° C. to about 185° C., 0.02 mmHg, to give (3.1 g, 63%) 4-[(4,5-dihydro-5,5-dimethyl-1H-imidazol-2-yl)methyl]-piperidine.

EXAMPLE 66

[2S-(2alpha,5alpha,6beta)]-6-[[[4-[(4,5-dihydro-5,5-dimethyl-1H-imidazol-2-yl)methyl]-1-piperidinyl]methylene]amino]-4-thia-1-azabicyclo[3.2.0]heptane-2-carboxylic acid hydrochloride By the procedure of Example 9, the product [2S-(2alpha,5alpha,6beta)]-6-[[[4-(4,5-dihydro-5,5-dimethyl-1H-imidazol-2-yl)methyl]-1-piperidinyl]methylene]amino]-4-thia-1-azabicyclo[3.2.0]heptane-2-carboxylic acid hydrochloride (1.2 g, 48% yield) was obtained from 4-[(4,5-dihydro-5,5-dimethyl-1H-imidazol-2-yl)methyl]-piperidine (1.4 g, 0.0068M) and 6-aminopenicillanic acid (1.1 g, 0.0055M).

EXAMPLE 67 rac-4-[2-(4,5-dihydro-1H-imidazol-2-yl)ethyl]hexahydro-1H-azepine

A mixture containing 2-cyanoethyl hexahydro-1H-azepine-1-carboxaldehyde (1.94 g, 0.01M) and ethylenediamine p-toluenesulfonate (5.4 g, 0.023M) was heated at 200° C. under nitrogen for 4½ hrs. The mixture was dissolved in ethanol (30 ml), basified with sodium ethoxide (0.024M), filtered and stripped to dryness. The residue was distilled at 180° to about 190° C., 0.05 mmHg to give rac-4-[2-(4,5-dihydro-1H-imidazol-2-yl)ethyl]hexahydro-1H-azepine (79% yield).

EXAMPLE 68

[2S-(2alpha,5alpha,6beta)]-6-[[[4-[2-(4,5-dihydro-1H-imidazol-2-yl)ethyl]hexahydro-1H-azepin-1-yl]-methylene]amino]-3,3-dimethyl-7-oxo-4-thia-1-azabicyclo[3.2.0]heptane-2-carboxylic acid hydrochloride A mixture containing rac-4-[2-(4,5-dihydro-1H-imidazol-2-yl)ethyl]hexahydro-1H-azepine (1.95 g, 0.01M), methanol (50 ml) and dimethylformamide dimethylacetal (36 ml) was heated at 90° C. for 8 hrs. The excess of dimethylformamide dimethylacetal was removed in vacuo to give 4-[2-(4,5-dihydro-1H-imidazol-2-yl)ethyl]hexahydro-1H-azepine-1-carboxaldehyde dimethylacetal to the mixture of 6-aminopenicillanic acid (1.95 g, 0.009M) and diisopropylethylamine (1.52 ml) in dry chloroform (25 ml) was added the solution fo the above hexahydroazepine carboxaldehyde dimethylacetal in dry chloroform (10 ml) at 0° C. The reaction was stirred at 0° C. for 1 hr. and at room temperature for 3 hrs. After the reaction solvent was removed and the residue dissolved in water (30 ml). The aqueous solution, washed with ethylacetate was acidified to pH 3 with dil. HCl and purified on Sephadex LH 20 columns to give [2S-(2alpha,5alpha,6beta)]-6-[[[4-[2-(4,5-dihydro-1H-imidazol-2-yl)ethyl]hexahydro-1H-azepin-1-yl]methylene]amino]-3,3-dimethyl-7-oxo-4-thia-1-azabicyclo[3.2.0]heptane-2-carboxylic acid hydrochloride (1.03 g, 27% yield).

EXAMPLE 69

The in vitro antibacterial activity of the following compounds:

| Compound | |
|---|---|
| A | [2S—(2alpha, 5alpha, 6beta)]-6-[[[4-(1H—imidazol-1-yl-methyl)-1-piperidinyl]methylene]amino-3,3-dimethyl-6-oxo-4-thia-1-azabicyclo[3.2.0]heptane-2-carboxylic acid |
| B | [2S—(2alpha, 5alpha, 6beta)]-6-[[[4-[2-(1H—imidazol-1-yl)ethyl]-1-piperidinyl]methylene]amino]-3,3-dimethyl-7-oxo-4-thia-1-azabicyclo[3.2.0]heptane-2-carboxylic acid hydrate hydrochloride |
| C | [2S—(2alpha, 5alpha, 6beta)]-6-[[4-[3-(1H—imidazol-1-yl)propyl-1-piperidinyl]methylene]amino]-3,3-dimethyl-7-oxo-4-thia-1-azabicyclo[3.2.0]heptane-2-carboxylic acid 1.2 mole hydrochloride monohydrate |
| D | [2S—(2alpha, 5alpha, 6beta)]-6-[[4-[hexahydro[2-(1H—imidazol-1-yl)ethyl]-1H—azepin-1-yl]methylene]amino-3,3-dimethyl-7-oxo-4-thia-1-azabicyclo[3.2.0]heptane-2-carboxylic acid 1.2 molar hydrochloride hydrate (diastereomers) |
| E | [2S—(2alpha, 5alpha, 6beta)]-6[[4-[3-[(2,4,5-trimethyl-1H—imidazol-1-yl)propyl]-1-piperidinyl]methlene]amino]-3,3-dimethyl-7-oxo-4-thia-1-azabicyclo[3.2.0]heptane-2-carboxylic acid hydrate hydrochloride |
| F | [2S—(2alpha, 5alpha, 6beta)]-3,3-dimethyl-6-[[[4-[3-(2-methyl-1H—imidazol-1-yl)propyl]-1-piperidinyl]methylene]amino]-7-oxo-4-thia-1-azabicyclo[3.2.0]heptane-2-carboxylic acid 1.15 molar hydrochloride 1.75 molar hydrate |
| G | [2S—(2alpha, 5alpha, 6beta)]-6-[[[4-[3-(2-ethyl-4-methyl-1H—imidazol-1-yl)propyl]piperidinyl]methylene]amino]-3,3-dimethyl-7-oxo-4-thia-1-azabicyclo[3.2.0]heptane-2-carboxylic acid hydrochloride |
| H | [2S—(2alpha, 5alpha, 6beta)]-6-[[[4-[(2-amino-1H—imidazol-1-yl)methyl-1-piperidinyl]methyl- |

| Com-pound | |
|---|---|
| | ene]amino]-3,3-dimethyl-7-oxo-4-thia-1-azabicy-clo[3.2.0]heptane-2-carboxylic acid hydrochloride |
| I | [2S—(2alpha, 5alpha, 6beta)]-6-[[[4-[3-(2-amino-1H—imidazol-1-yl)propyl]piperidinyl]methylene]amino]-3,3-dimethyl-7-oxo-4-thia-1-azabicyclo[3.2.0]heptane-2-carboxylic acid hydrochloride |
| J | [2S—(2alpha, 5alpha, 6beta)]-6-[[[4-[[2-(aminomethyl)-1H—imidazol-1-yl]methyl]-1-piperidinyl]methylene]amino]-3,3-dimethyl-7-oxo-4-thia-1-azabicyclo[3.2.0]-heptane-2-carboxylic acid hydrochloride |
| K | [2S—(2alpha, 5alpha, 6beta)]-6-[[[4-[3-(2-nitro-1H—imidazol-1-yl)]piperidinyl]methylene]amino]-3,3-dimethyl-7-oxo-4-thia-1-azabicyclo[3.2.0]heptane-2-carboxylic acid hydrochloride .66 molar hydrate |
| L | [2S—(2alpha, 5alpha, 6beta)]-6-[[[4-(4,5-dihydro-1H—imidazol-2-yl)-1-piperidinyl]methylene]amino]-3,3-dimethyl-7-oxo-4-thia-1-azabicyclo[3.2.0]heptane-2-carboxylic acid hydrochloride |
| M | [2S—(2alpha, 5alpha, 6beta)]-6-[[[4-[(4,5-dihydro-1H—imidazol-2-yl)methyl]-1-piperidinyl]methylene]amino]-3,3-dimethyl-7-oxo-4-thia-1-azabicyclo[3.2.0]heptane-2-carboxylic acid hydrochloride |
| N | [2S—(2alpha, 5alpha, 6beta)]-6-[[[4-[4,5-dihydro-1H—imidazol-2-yl)ethyl]-1-piperidinyl]methylene]amino]-3,3-dimethyl-7-oxo-4-thia-1-azabicyclo[3.2.0]heptane-2-carboxylic acid hydrochloride |
| O | [2S—(2alpha, 5alpha, 6beta)]-6-[[[4-(1H—imidazol-2-yl-1-piperidinyl]methylene]amino]-3,3-dimethyl-7-oxo-4-thia-1-azabicyclo[3.2.0]heptane-2-carboxylic acid hydrochloride trihydrate |
| P | [2S—(2alpha, 5alpha, 6beta)]-6-[[[3-(1H—imidazol-2-yl)-1-piperidinyl]methylene]amino]-3,3-dimethyl-7-oxo-4-thia-1-azabicyclo[3.2.0]heptane-2-carboxylic acid hydrochloride |
| Q | [2S—(2alpha, 5alpha, 6beta)]-6-[[[4-(1H—imidazol-2-yl-methyl)-1-piperidinyl]methylene]amino]-3,3-dimethyl-7-oxo-4-thia-1-azabicyclo[3.2.0]heptane-2-carboxylic acid hydrochloride |
| R | [2S—(2alpha, 5alpha, 6beta)]-6-[[[4-[3-[2-(hydroxymethyl)-1H—imidazol-1-yl]propyl-1-piperidinyl]methylene]amino]-3,3-dimethyl-7-oxo-4-thia-1-azabicyclo[3.2.0]heptane-2-carboxylic acid hydrochloride 1.1 molar hydrate |
| S | [2S—(2alpha, 5alpha, 6beta)]-6-[[[4-[3-[2-[[(dimethyl-amino)methylene]amino]-1H—imidazol-1-yl]propyl]-1-piperidinyl]methylene]amino]-3,3-dimethyl-7-oxo-4-thia-1-azabicyclo[3.2.0]heptane-2-carboxylic acid 1.7 molar hydrochloride 2.6 molar hydrate |
| U | [2S—(2alpha, 5alpha, 6beta)]-6-[[[4-[(1,4,5,6-tetrahydro-2-pyrimidinyl)methyl]-1-piperidinyl]methylene]amino]-3,3-dimethyl-7-oxo-4-thia-1-azabicyclo[3.2.0]heptane-2-carboxylic acid hydrochloride | as compared to an amdinocillin (mecillinam) were tested by the following procedure:

Drug dilutions are prepared in Mueller-Hinton broth ranging from 128 to 0.008 μg/ml. The diluted agents are dispensed in 100 μl amounts into the wells of a 96-well tray and used immediately or frozen at −10° to −70° C. until needed. Using an automated inoculator, 1.5 μl of a $10^{-2}$ dilution of an overnight culture is added to each well of the tray. The tops of the trays are then sealed using transparent tape and incubated overnight at 37° C. The trays are examined with the aid of a viewer. The lowest concentration at which no growth is observed is considered to be the minimum inhibitory concentration (MIC).

TABLE 1

| Organisms | In Vitro MIC: μg/ml | | | | |
|---|---|---|---|---|---|
| | A | B | C | D | Amdinocillin |
| E. coli 257 | 0.125 | 0.25 | 2 | 0.125 | 0.125 |
| E. coli 48 | 0.062 | 0.25 | 2 | 0.125 | 0.062 |
| E. coli 4 | 0.062 | 8 | 8 | 0.125 | 0.062 |
| E. coli 387–1 | 0.125 | 8 | 8 | 0.125 | 0.031 |
| E. coli R-563 | 0.125 | 8 | 4 | 0.125 | 0.125 |
| E. coli 503–455 | 2 | 1 | 128 | 1 | 2 |
| E. coli 5152 | 16 | 16 | >128 | 16 | 8 |
| K. pneumoniae A | <0.008 | 0.062 | 4 | 0.031 | 0.031 |
| K. pneumoniae HE7 | >128 | >128 | >128 | >128 | >128 |
| K. pneumoniae 503–964 | 0.016 | 0.25 | 8 | 0.25 | 0.125 |
| K. pneumoniae 4964 | 2 | 0.5 | >128 | 1 | 64 |
| K. pneumoniae 5096 | 64 | 0.25 | >128 | >128 | 128 |

TABLE 1-continued

| Organisms | In Vitro MIC: µg/ml | | | | | |
|---|---|---|---|---|---|---|
| | A | B | C | D | Amdinocillin | |
| K. pneumoniae 35 | 0.25 | 1 | 8 | 0.25 | 0.125 | |
| K. pneumoniae 503-994 | 0.25 | 0.25 | 32 | 0.125 | 0.062 | |
| K. pneumoniae 8357 | 0.25 | 0.25 | 16 | 0.25 | 0.25 | |
| E. cloacae 6951 | 4 | 16 | >128 | 16 | 16 | |
| E. cloacae 9570A | 0.5 | 0.5 | 16 | 0.5 | 0.125 | |
| E. cloacae 5699 | 0.5 | 0.5 | 16 | 0.5 | 0.25 | |
| E. cloacae 9295 | 0.5 | 0.5 | 16 | 0.5 | 0.25 | |
| E. cloacae 24 | 0.5 | 2 | 32 | 0.5 | 0.125 | |
| E. cloacae P99 | 0.25 | — | 8 | 0.125 | 0.062 | |
| E. cloacae 214 | 0.125 | 1 | 16 | 0.25 | 0.125 | |
| E. aerogenes 8 | 32 | 0.25 | >128 | 128 | 128 | |
| E. aerogenes 83 | 2 | 0.5 | >128 | 16 | 8 | |
| E. aerogenes 503-478 | 0.062 | 2 | 128 | 8 | 4 | |
| C. freundii CDC6 | 0.125 | 0.25 | 16 | 0.25 | 0.125 | 0.062 |
| C. freundii 8 ASM | 0.062 | 0.062 | 4 | 0.062 | 0.062 | 0.031 |
| C. diversus CDC 1663-72 | 0.125 | 0.25 | 4 | 0.125 | 0.062 | 0.062 |
| S. typhi P58A | 0.25 | 0.062 | 8 | 0.125 | 0.062 | 0.062 |
| S. schottmuelleri | 0.125 | 0.25 | 4 | 0.125 | 0.062 | 0.031 |
| P. vulgaris 100 | 8 | 8 | >128 | 16 | 0.5 | 0.5 |
| P. vulgaris 101 | 16 | 1 | 128 | 32 | 64 | 0.25 |
| P. vulgaris ATCC 6380 | 0.125 | 0.5 | 4 | 0.125 | 0.031 | 0.062 |
| P. rettgeri ATCC 9250 | 0.5 | 0.5 | 16 | 0.5 | 0.125 | 0.062 |
| P. mirabilis 503-1136 | 8 | 8 | 128 | 16 | 2 | 0.5 |
| P. mirabilis 620A | 16 | >128 | >128 | 64 | 64 | 16 |
| P. mirabilis 2 | 0.5 | 1 | 16 | 0.5 | 0.25 | 0.062 |
| P. mirabilis 90 | 1 | 2 | 32 | 1 | 0.25 | 0.25 |
| P. mirabilis 190 | 0.25 | 0.5 | 8 | 0.25 | 0.125 | 0.031 |
| S. marcescens 5805 | 1 | 1 | 32 | 2 | 1 | 1 |
| S. marcescens SM | 0.25 | 0.25 | 8 | 0.25 | 0.125 | 0.062 |
| S. marcescens S1 | 0.25 | 0.5 | 128 | 0.5 | 0.25 | 0.125 |
| S. marcescens S2 | 0.25 | 0.5 | 16 | 0.5 | 0.25 | 0.125 |
| S. marcescens S3 | 0.25 | 0.5 | 16 | 0.5 | 0.125 | 0.062 |
| S. marcescens S4 | 1 | 1 | 32 | 1 | 1 | 0.5 |
| S. marcescens S5 | 2 | 2 | 64 | 2 | 1 | 1 |
| S. marcescens S147 | 0.25 | 0.5 | 16 | 0.125 | 0.125 | 0.062 |
| S. marcescens S714 | 1 | 1 | 32 | 1 | 0.5 | 0.5 |
| P. aeruginosa B | 0.25 | >128 | 8 | 0.25 | 0.125 | >128 |
| P. aeruginosa Stone 130 | >128 | — | >128 | >128 | >128 | — |
| P. aeruginosa POW 151 | >128 | >128 | >128 | >128 | >128 | >128 |
| P. aeruginosa 8710 | >128 | >128 | >128 | >128 | >128 | >128 |
| P. aeruginosa 503-56 | >128 | — | >128 | >128 | >128 | — |
| P. aeruginosa 503-820 | >128 | >128 | >128 | >128 | >128 | 128 |
| P. aeruginosa 5700 | 0.25 | >128 | 16 | 0.5 | 0.25 | >128 |
| P. aeruginosa 5712 | >128 | >128 | >128 | >128 | >128 | >128 |
| P. aeruginosa 8780 | >128 | >128 | >128 | >128 | >128 | >128 |
| P. aeruginosa 6148B | >128 | — | >128 | >128 | >128 | — |
| S. faecalis C1 | 128 | >128 | >128 | >128 | >128 | >128 |
| S. pyogenes 4 | 1 | — | 64 | 1 | 1 | — |
| S. pyogenes 503-782 | 128 | 8 | >128 | >128 | >128 | 1 |
| S. pneumoniae SC | 2 | — | 64 | 4 | 2 | — |
| S. pneumoniae 6301 | 1 | 4 | 128 | 4 | 2 | 1 |
| S. pneumoniae 6302 | 2 | — | 128 | 8 | 4 | — |
| S. aureus Giorgio | 8 | 32 | >128 | 16 | 32 | 32 |
| S. aureus 1059B | 32 | >128 | >128 | 128 | 128 | 128 |
| S. aureus Smith | 8 | — | >128 | 32 | 32 | — |

TABLE 2

| Organisms | In Vitro MIC: µg/ml | | | | | |
|---|---|---|---|---|---|---|
| | C | F | G | E | | Amdinocillin |
| E. coli 257 | 2 | 0.125 | 0.25 | 0.062 | 0.125 | <0.008 |
| E. coli 48 | 2 | 0.062 | 0.062 | 0.062 | 0.062 | 0.016 |
| E. coli 4 | 8 | 0.062 | 0.25 | 4 | 0.062 | 2 |
| E. coli 387-1 | 8 | 0.125 | 0.25 | 4 | 0.031 | 2 |
| E. coli R-563 | 4 | 0.062 | 0.25 | 4 | 0.125 | 4 |
| E. coli 503-455 | 128 | 2 | 4 | 2 | 2 | 1 |
| E. coli 5152 | >128 | 8 | 16 | 8 | 8 | 16 |
| K. pneumoniae A | 4 | 0.031 | 0.125 | 0.062 | 0.031 | <0.008 |
| K. pneumoniae HE7 | >128 | >128 | >128 | >128 | >128 | >128 |
| K. pneumoniae 503-964 | 8 | 4 | 0.062 | 0.062 | 0.125 | 0.062 |
| K. pneumoniae 4964 | >128 | 32 | 2 | 1 | 64 | 0.062 |
| K. pneumoniae 5096 | >128 | 64 | 128 | >128 | 128 | >128 |
| K. pneumoniae 35 | 8 | 0.125 | 0.5 | 0.125 | 0.125 | 0.062 |
| K. pneumoniae 503-994 | 32 | 2 | 0.25 | 0.062 | 0.062 | 0.062 |
| K. pneumoniae 8357 | 16 | 1 | 1 | 0.062 | 0.25 | 0.062 |
| E. cloacae 6951 | >128 | 8 | 16 | 8 | 16 | 8 |

TABLE 2-continued

| Organisms | In Vitro MIC: μg/ml | | | | | |
|---|---|---|---|---|---|---|
| | C | F | G | E | Amdinocillin | |
| E. cloacae 9570A | 16 | 0.25 | 0.5 | 0.125 | 0.125 | 0.125 |
| E. cloacae 5699 | 16 | 0.25 | 0.5 | 0.125 | 0.25 | 0.062 |
| E. cloacae 9295 | 16 | 0.25 | 0.5 | 0.25 | 0.25 | 0.125 |
| E. cloacae 24 | 32 | 0.25 | 0.5 | 0.5 | 0.125 | 0.5 |
| E. cloacae P99 | 8 | 0.125 | 0.5 | 0.125 | 0.062 | 0.062 |
| E. cloacae 214 | 16 | 0.125 | 0.25 | 0.5 | 0.125 | 0.5 |
| E. aerogenes 8 | >128 | 32 | 16 | 32 | 128 | 128 |
| E. aerogenes 83 | >128 | 16 | 0.5 | 0.5 | 8 | 4 |
| E. aerogenes 503-478 | 128 | 4 | 8 | 1 | 4 | 1 |
| C. freundii CDC6 | 16 | 0.062 | 0.25 | 0.125 | 0.125 | 0.062 |
| C. freundii 8 ASM | 4 | 0.062 | 0.125 | <0.008 | 0.062 | <0.008 |
| C. diversus CDC 1663-72 | 4 | 0.062 | 0.125 | 0.062 | 0.062 | 0.062 |
| S. typhi P58A | 8 | 0.062 | 0.25 | 0.062 | 0.062 | 0.016 |
| S. schottmuelleri | 4 | 0.062 | 0.125 | 0.062 | 0.062 | <0.008 |
| P. vulgaris 100 | >128 | 16 | 32 | 8 | 0.5 | 0.5 |
| P. vulgaris 101 | 128 | 16 | 16 | 4 | 64 | 0.5 |
| P. vulgaris ATCC 6380 | 4 | 0.25 | 0.25 | 0.062 | 0.031 | <0.008 |
| P. rettgeri ATCC 9250 | 16 | 0.25 | 1 | 0.5 | 0.125 | <0.008 |
| P. mirabilis 503-1136 | 128 | 8 | 16 | 4 | 2 | 1 |
| P. mirabilis 620A | >128 | 16 | 64 | 128 | 64 | 32 |
| P. mirabilis 2 | 16 | 0.5 | 1 | 0.5 | 0.25 | 0.125 |
| P. mirabilis 90 | 32 | 0.5 | 1 | 0.5 | 0.25 | 0.5 |
| P. mirabilis 190 | 8 | 0.25 | 0.5 | 0.25 | 0.125 | 0.062 |
| S. marcescens 5805 | 32 | 0.5 | 4 | 0.5 | 1 | 1 |
| S. marcescens SM | 8 | 0.125 | 1 | 0.125 | 0.125 | 0.062 |
| S. marcescens S1 | 128 | 0.5 | 1 | 1 | 0.25 | 0.062 |
| S. marcescens S2 | 16 | 0.25 | 1 | 0.5 | 0.25 | 0.125 |
| S. marcescens S3 | 16 | 0.25 | 1 | 0.25 | 0.125 | 0.125 |
| S. marcescens S4 | 32 | 2 | 2 | 0.5 | 1 | 0.5 |
| S. marcescens S5 | 64 | 1 | 2 | 1 | 1 | 1 |
| S. marcescens S147 | 16 | 0.25 | 1 | 0.5 | 0.125 | 0.125 |
| S. marcescens S714 | 32 | 1 | 8 | 1 | 0.5 | 2 |
| P. aeruginosa B | 8 | 0.25 | 0.25 | >128 | 0.125 | >128 |
| P. aeruginosa Stone 130 | >128 | >128 | >128 | >128 | >128 | >128 |
| P. aeruginosa POW 151 | >128 | >128 | >128 | >128 | >128 | >128 |
| P. aeruginosa 8710 | >128 | >128 | >128 | >128 | >128 | >128 |
| P. aeruginosa 503-56 | >128 | >128 | >128 | >128 | >128 | >128 |
| P. aeruginosa 503-820 | >128 | >128 | >128 | >128 | >128 | >128 |
| P. aeruginosa 5700 | 16 | 0.5 | 1 | >128 | 0.25 | 128 |
| P. aeruginosa 5712 | >128 | >128 | >128 | >128 | >128 | >128 |
| P. aeruginosa 8780 | >128 | >12 | >128 | >128 | >128 | >128 |
| P. aeruginosa 6148B | >128 | >128 | >128 | >128 | >128 | 128 |
| S. faecalis C1 | >128 | 128 | 128 | 128 | >128 | >128 |
| S. pyogenes 4 | 64 | 0.5 | 1 | 0.5 | 1 | 1 |
| S. pyogenes 503-782 | >128 | 128 | 128 | 128 | >128 | >128 |
| S. pneumoniae SC | 64 | 1 | 1 | 0.5 | 2 | 1 |
| S. pneumoniae 6301 | 128 | 1 | 1 | 1 | 2 | 2 |
| S. pneumoniae 6302 | 128 | 2 | 2 | 1 | 4 | 2 |
| S. aureus Giorgio | >128 | 8 | 8 | 8 | 32 | 32 |
| S. aureus 1059B | >128 | 64 | 128 | 64 | 128 | 128 |
| S. aureus Smith | >128 | 8 | 8 | 8 | 32 | 16 |

TABLE 3

| Organisms | In Vitro MIC: μg/ml | | | | | |
|---|---|---|---|---|---|---|
| | H | I | J | K | Amdinocillin | |
| E. coli 257 | 0.25 | 0.031 | 0.125 | 0.5 | 0.125 | 0.062 |
| E. coli 48 | 0.062 | 0.031 | 8 | 0.25 | 0.062 | 4 |
| E. coli 4 | 0.062 | 0.031 | 0.062 | 0.5 | 0.062 | 0.062 |
| E. coli 387-1 | 0.125 | 0.062 | 0.125 | 0.5 | 0.031 | 0.062 |
| E. coli R-563 | 0.062 | 0.062 | 0.125 | 0.5 | 0.125 | 0.062 |
| E. coli 503-455 | 1 | 1 | 1 | 4 | 2 | 0.25 |
| E. coli 5152 | 8 | 4 | 16 | 8 | 8 | 8 |
| K. pneumoniae A | 0.031 | <0.008 | 0.062 | 0.25 | 0.031 | 0.062 |
| K. pneumoniae HE7 | 128 | >128 | >128 | 64 | >128 | 64 |
| K. pneumoniae 503-964 | 0.125 | 0.062 | 0.25 | 0.5 | 0.125 | 0.062 |
| K. pneumoniae 4964 | 64 | 0.25 | 0.5 | 0.5 | 64 | 0.062 |
| K. pneumoniae 5096 | 64 | >128 | 128 | 16 | 128 | 32 |
| K. pneumoniae 35 | 0.25 | 0.25 | 0.5 | 0.5 | 0.125 | 0.062 |
| K. pneumoniae 503-994 | 0.125 | 0.062 | 8 | 0.25 | 0.062 | 8 |
| K. pneumoniae 8357 | 0.125 | 0.062 | 4 | 2 | 0.25 | 8 |
| E. cloacae 6951 | 4 | 8 | 16 | 16 | 16 | 4 |
| E. cloacae 9570A | 0.25 | 0.125 | 0.5 | 1 | 0.125 | 0.062 |
| E. cloacae 5699 | 0.25 | 0.062 | 4 | 1 | 0.25 | 2 |
| E. cloacae 9295 | 0.5 | 0.125 | 4 | 1 | 0.25 | 4 |
| E. cloacae 24 | 0.25 | 0.125 | 0.5 | 1 | 0.125 | 0.062 |

TABLE 3-continued

| Organisms | In Vitro MIC: μg/ml | | | | | |
|---|---|---|---|---|---|---|
| | H | I | J | K | | Amdinocillin |
| E. cloacae P99 | 0.062 | 0.031 | 8 | 0.5 | 0.062 | 8 |
| E. cloacae 214 | 0.125 | 0.062 | 1 | 0.5 | 0.125 | 2 |
| E. aerogenes 8 | 32 | 128 | 0.5 | 8 | 128 | 0.25 |
| E. aerogenes 83 | 16 | 1 | 1 | 8 | 8 | 4 |
| E. aerogenes 503-478 | 8 | 1 | 8 | 4 | 4 | 8 |
| C. freundii CDC6 | 0.062 | 0.031 | 64 | 0.5 | 0.125 | 32 |
| C. freundii 8 ASM | 0.031 | 0.031 | 0.125 | 0.25 | 0.062 | 0.006 |
| C. diversus CDC 1663-72 | 0.062 | 0.031 | 0.031 | 0.25 | 0.062 | 0.062 |
| S. typhi P58A | 0.062 | 0.062 | 8 | 0.5 | 0.062 | 8 |
| S. schottmuelleri | 0.062 | 0.031 | 0.062 | 0.5 | 0.062 | 0.062 |
| P. vulgaris 100 | 4 | 4 | 8 | 16 | 0.5 | 0.5 |
| P. vulgaris 101 | 8 | 128 | 8 | 16 | 64 | 8 |
| P. vulgaris ATCC 6380 | 0.062 | 0.062 | 0.125 | 0.5 | 0.031 | 0.016 |
| P. rettgeri ATCC 9250 | 0.25 | 0.25 | 16 | 2 | 0.125 | 8 |
| P. mirabilis 503-1136 | 4 | 4 | 8 | 8 | 2 | 8 |
| P. mirabilis 620A | 16 | 32 | >128 | 16 | 64 | 8 |
| P. mirabilis 2 | 0.25 | 0.25 | 8 | 4 | 0.25 | 8 |
| P. mirabilis 90 | 0.125 | 4 | 1 | 8 | 0.25 | 0.25 |
| P. mirabilis 190 | 0.125 | 0.125 | 0.5 | 0.5 | 0.125 | 0.062 |
| S. marcescens 5805 | 0.5 | 0.25 | 1 | 8 | 1 | 0.5 |
| S. marcescens SM | 0.125 | 0.062 | 0.5 | 2 | 0.125 | 0.062 |
| S. marcescens S1 | 0.125 | 0.062 | 0.5 | 2 | 0.25 | 0.125 |
| S. marcescens S2 | 0.062 | 0.062 | 0.25 | 2 | 0.25 | 0.125 |
| S. marcescens S3 | 0.125 | 0.062 | 0.25 | 4 | 0.125 | 0.062 |
| S. marcescens S4 | 0.5 | 0.25 | 1 | 8 | 1 | 0.5 |
| S. marcescens S5 | 0.5 | 0.25 | 0.5 | 8 | 1 | 0.5 |
| S. marcescens S147 | 0.031 | 0.062 | 0.25 | 2 | 0.125 | 0.062 |
| S. marcescens S714 | 0.25 | 0.125 | 0.5 | 8 | 0.5 | 0.5 |
| P. aeruginosa B | 0.5 | 0.062 | 0.25 | 0.25 | 0.125 | 0.062 |
| P. aeruginosa Stone 130 | >128 | >128 | >128 | >128 | >128 | 128 |
| P. aeruginosa POW 151 | >128 | >128 | >128 | >128 | >128 | >128 |
| P. aeruginosa 8710 | 128 | 128 | >128 | >128 | >128 | 128 |
| P. aeruginosa 503-56 | 32 | 128 | 64 | >128 | >128 | 128 |
| P. aeruginosa 503-820 | 64 | 128 | >128 | >128 | >128 | 64 |
| P. aeruginosa 5700 | 0.125 | 0.062 | 0.5 | 4 | 0.25 | 0.062 |
| P. aeruginosa 5712 | 128 | >128 | >128 | >128 | >128 | >128 |
| P. aeruginosa 8780 | >128 | >128 | >128 | >128 | >128 | >128 |
| P. aeruginosa 6148B | 64 | 128 | 128 | >128 | >128 | 64 |
| S. faecalis C1 | 64 | >128 | 128 | 128 | >128 | 128 |
| S. pyogenes 4 | 1 | 1 | 4 | 0.5 | 1 | 2 |
| S. pyogenes 503-782 | 64 | >128 | 128 | 128 | >128 | 128 |
| S. pneumoniae SC | 1 | 4 | 4 | 1 | 2 | 2 |
| S. pneumoniae 6301 | 1 | 2 | 1 | 1 | 2 | 2 |
| S. pneumoniae 6302 | 1 | 4 | 4 | 1 | 4 | 2 |
| S. aureus Giorgio | 8 | 16 | 8 | 8 | 32 | 8 |
| S. aureus 1059B | 128 | 64 | >128 | 128 | 128 | 64 |
| S. aureus Smith | 8 | 16 | 8 | 8 | 32 | 8 |

TABLE 4

| Organisms | In Vitro MIC: μg/ml | | | |
|---|---|---|---|---|
| | L | M | N | Amdinocillin |
| E. coli 257 | 1 | 0.125 | 0.031 | 0.125 |
| E. coli 48 | 0.5 | 0.125 | 0.031 | 0.062 |
| E. coli 4 | 0.125 | 0.062 | 0.016 | 0.062 |
| E. coli 387-1 | 387-1 | 0.062 | 0.016 | 0.031 |
| E. coli R-563 | 0.25 | 0.062 | 0.031 | 0.125 |
| E. coli 503-455 | 4 | 2 | 1 | 2 |
| E. coli 5152 | 32 | 16 | 8 | 8 |
| K. pneumoniae A | 0.25 | 0.062 | 0.016 | 0.031 |
| K. pneumoniae HE7 | >128 | >128 | >128 | >128 |
| K. pneumoniae 503-964 | 2 | 0.25 | 0.062 | 0.125 |
| K. pneumoniae 4964 | 64 | 2 | 32 | 64 |
| K. pneumoniae 5096 | 64 | >128 | >128 | 128 |
| K. pneumoniae 35 | 2 | 1 | 0.125 | 0.125 |
| K. pneumoniae 503-994 | 1 | 0.25 | 0.062 | 0.062 |
| K. pneumoniae 8357 | 2 | 1 | 0.125 | 0.25 |
| E. cloacae 6951 | 8 | 32 | 8 | 16 |
| E. cloacae 9570A | 2 | 0.25 | 0.062 | 0.125 |
| E. cloacae 5699 | 1 | 0.25 | 0.062 | 0.25 |
| E. cloacae 9295 | 2 | 0.5 | 0.125 | 0.25 |
| E. cloacae 24 | 1 | 0.5 | 0.125 | 0.125 |
| E. cloacae P99 | 0.25 | 0.062 | 0.016 | 0.062 |
| E. cloacae 214 | 1 | 0.25 | 0.062 | 0.125 |
| E. aerogenes 8 | 32 | 32 | 32 | 128 |
| E. aerogenes 83 | 2 | 2 | 8 | 8 |
| E. aerogenes 503-478 | 8 | 4 | 4 | 4 |
| C. freundii CDC6 | 0.5 | 0.125 | 0.031 | 0.125 |
| C. freundii 8 ASM | 0.25 | 0.062 | 0.031 | 0.062 |
| C. diversus CDC 1663-72 | 0.5 | 0.062 | 0.031 | 0.062 |
| S. typhi P58A | 0.5 | 0.062 | 0.031 | 0.062 |
| S. schottmuelleri | 0.25 | 0.062 | 0.031 | 0.062 |
| P. vulgaris 100 | 32 | 8 | 0.5 | 0.5 |
| P. vulgaris 101 | 32 | 16 | 64 | 64 |
| P. vulgaris ATCC 6380 | 0.25 | 0.25 | 0.031 | 0.031 |
| P. rettgeri ATCC 9250 | 1 | 0.5 | 0.125 | 0.125 |
| P. mirabilis 503-1136 | 8 | 8 | 4 | 2 |
| P. mirabilis 620A | >128 | >128 | 128 | 64 |
| P. mirabilis 2 | 1 | 0.5 | 0.125 | 0.25 |
| P. mirabilis 90 | 2 | 0.5 | 0.125 | 0.25 |
| P. mirabilis 190 | 0.5 | 0.5 | 0.125 | 0.125 |
| S. marcescens 5805 | 8 | 1 | 0.25 | 1 |
| S. marcescens SM | 1 | 0.125 | 0.062 | 0.125 |
| S. marcescens S1 | 0.5 | 0.25 | 2 | 0.25 |
| S. marcescens S2 | 0.5 | 0.25 | 0.062 | 0.25 |
| S. marcescens S3 | 0.5 | 0.125 | 0.062 | 0.125 |
| S. marcescens S4 | 2 | 1 | 0.25 | 1 |
| S. marescens S5 | 4 | 1 | 0.25 | 1 |
| S. marcescens S147 | 1 | 0.25 | 0.062 | 0.125 |

TABLE 4-continued

| Organisms | In Vitro MIC: µg/ml | | | |
|---|---|---|---|---|
| | L | M | N | Amdinocillin |
| S. marcescens S714 | 2 | 0.5 | 0.125 | 0.5 |
| P. aeruginosa B | 0.5 | 0.25 | 0.062 | 0.125 |
| P. aeruginosa Stone 130 | >128 | >128 | >128 | >128 |
| P. aeruginosa POW 151 | >128 | >128 | >128 | >128 |
| P. aeruginosa 8710 | 128 | 64 | 32 | >128 |
| P. aeruginosa 503-56 | 64 | 32 | 16 | >128 |
| P. aeruginosa 503-820 | 128 | 64 | 16 | >128 |
| P. aeruginosa 5700 | 2 | 0.125 | 0.062 | 0.25 |
| P. aeruginosa 5712 | >128 | 128 | 64 | >128 |
| P. aeruginosa 8780 | >128 | 128 | 128 | >128 |
| P. aeruginosa 6148B | 128 | 32 | 32 | >128 |
| S. faecalis C1 | 32 | 32 | 64 | >128 |
| S. pyogenes 4 | 0.5 | 1 | 1 | 1 |
| S. pyogenes 503-782 | 32 | 32 | 64 | >128 |
| S. pneumoniae SC | 1 | 1 | 1 | 2 |
| S. pneumoniae 6301 | 0.5 | 1 | 1 | 2 |
| S. pneumoniae 6302 | 1 | 1 | 2 | 4 |
| S. aureus Giorgio | 2 | 2 | 8 | 32 |
| S. aureus 1059B | 64 | 32 | 64 | 128 |
| S. aureus Smith | 4 | 4 | 8 | 32 |

TABLE 5

| Organisms | In Vitro MIC: µg/ml | | |
|---|---|---|---|
| | O | P | Amdinocillin |
| E. coli 257 | 0.125 | 2 | 0.125 |
| E. coli 48 | 0.125 | 2 | 0.062 |
| E. coli 4 | 0.125 | 2 | 0.062 |
| E. coli 387-1 | 0.125 | 4 | 0.031 |
| E. coli R-563 | 0.125 | 2 | 0.125 |
| E. coli 503-455 | 1 | 64 | 2 |
| E. coli 5152 | 16 | >128 | 8 |
| K. pneumoniae A | 0.062 | 2 | 0.031 |
| K. pneumoniae HE7 | >128 | 128 | >128 |
| K. pneumoniae 503-964 | 0.5 | 8 | 0.125 |
| K. pneumoniae 4964 | 64 | 64 | 64 |
| K. pneumoniae 5096 | 64 | 64 | 128 |
| K. pneumoniae 35 | 1 | 16 | 0.125 |
| K. pneumoniae 503-994 | 0.5 | 8 | 0.062 |
| K. pneumoniae 8357 | 0.5 | 8 | 0.25 |
| E. cloacae 6951 | 16 | >128 | 16 |
| E. cloacae 9570A | 0.5 | 8 | 0.125 |
| E. cloacae 5699 | 0.5 | 8 | 0.25 |
| E. cloacae 9295 | 1 | 8 | 0.25 |
| E. cloacae 24 | 1 | 8 | 0.125 |
| E. cloacae P99 | 0.062 | 8 | 0.062 |

TABLE 5-continued

| Organisms | In Vitro MIC: µg/ml | | |
|---|---|---|---|
| | O | P | Amdinocillin |
| E. cloacae 214 | 0.5 | 8 | 0.125 |
| E. aerogenes 8 | 32 | 16 | 128 |
| E. aerogenes 83 | 8 | 8 | 8 |
| E. aerogenes 503-478 | >128 | >128 | 4 |
| C. freundii CDC6 | 0.125 | 4 | 0.125 |
| C. freundii 8 ASM | 0.062 | 2 | 0.062 |
| C. diversus CDC 1663-72 | 0.125 | 2 | 0.062 |
| S. typhi P58A | 0.125 | 2 | 0.062 |
| S. schottmuelleri | 0.125 | 2 | 0.062 |
| P. vulgaris 100 | 8 | 128 | 0.5 |
| P. vulgaris 101 | 32 | 64 | 64 |
| P. vulgaris ATCC 6380 | 0.25 | 0.5 | 0.031 |
| P. rettgeri ATCC 9250 | 0.5 | 4 | 0.125 |
| P. mirabilis 503-1136 | 4 | 64 | 2 |
| P. mirabilis 620A | 4 | >128 | 64 |
| P. mirabilis 2 | 1 | 8 | 0.25 |
| P. mirabilis 90 | 0.5 | 8 | 0.25 |
| P. mirabilis 190 | 0.5 | 4 | 0.125 |
| S. marcescens 5805 | 8 | 128 | 1 |
| S. marcesens SM | 0.5 | 8 | 0.125 |
| S. marcescens S1 | 0.5 | 8 | 0.25 |
| S. marcescens S2 | 0.5 | 8 | 0.25 |
| S. marcescens S3 | 0.25 | 8 | 0.125 |
| S. marcescens S4 | 2 | >128 | 1 |
| S. marcescens S5 | 4 | >128 | 1 |
| S. marcescens S147 | 0.25 | 8 | 0.125 |
| S. marcescens S714 | 1 | 32 | 0.5 |
| P. aeruginosa B | 0.5 | 8 | 0.125 |
| P. aeruginosa Stone 130 | >128 | >128 | >128 |
| P. aeruginosa POW 151 | >128 | >128 | >128 |
| P. aeruginosa 8710 | >128 | >128 | >128 |
| P. aeruginosa 503-56 | >128 | >128 | >128 |
| P. aeruginosa 503-820 | >128 | >128 | >128 |
| P. aeruginosa 5700 | 0.5 | 8 | 0.25 |
| P. aeruginosa 5712 | >128 | >128 | >128 |
| P. aeruginosa 8780 | >128 | >128 | >128 |
| P. aeruginosa 6148B | >128 | >128 | >128 |
| S. faecalis C1 | 32 | 64 | >128 |
| S. pyogenes 4 | 0.5 | 0.5 | 1 |
| S. pyogenes 503-782 | 32 | 64 | >128 |
| S. pneumoniae SC | 1 | 1 | 2 |
| S. pneumoniae 6301 | 1 | 1 | 2 |
| S. pneumoniae 6302 | 1 | 1 | 4 |
| S. aureus Giorgio | 4 | 4 | 32 |
| S. aureus 1059B | >128 | 64 | 128 |
| S. aureus Smith | 4 | 2 | 32 |

TABLE 6

| Organisms | In Vitro MIC: µg/ml | | | | | |
|---|---|---|---|---|---|---|
| | O | L | Q | M | | Amdinocillin |
| E. coli 257 | 0.125 | 1 | 0.062* | 0.125 | 0.125 | 0.062 |
| E. coli 48 | 0.125 | 0.5 | 8 | 0.125 | 0.062 | 4 |
| E. coli 4 | 0.125 | 0.125 | 0.062 | 0.062 | 0.062 | 0.062 |
| E. coli 387-1 | 0.125 | 0.25 | 0.062 | 0.062 | 0.031 | 0.062 |
| E. coli R-563 | 0.125 | 0.25 | 0.062 | 0.062 | 0.125 | 0.062 |
| E. coli 503-455 | 1 | 4 | 1 | 2 | 2 | 0.25 |
| E. coli 5152 | 16 | 32 | 64 | 16 | 8 | 8 |
| K. pneumoniae A | 0.062 | 0.25 | 0.062 | 0.062 | 0.031 | 0.062 |
| K. pneumoniae HE7 | >128 | >128 | >128 | >128 | >128 | 64 |
| K. pneumoniae 503-964 | 0.5 | 2 | 0.5 | 0.25 | 0.125 | 0.062 |
| K. pneumoniae 4964 | 64 | 64 | 4 | 2 | 64 | 0.062 |
| K. pneumoniae 5096 | 64 | 64 | 128 | >128 | 128 | 32 |
| K. pneumoniae 35 | 1 | 2 | 0.25 | 1 | 0.125 | 0.062 |
| K. pneumoniae 503-994 | 0.5 | 1 | 8 | 0.25 | 0.062 | 8 |
| K. pneumoniae 8357 | 0.5 | 2 | 4 | 1 | 0.25 | 8 |
| E. cloacae 6951 | 16 | 8 | 16 | 32 | 16 | 4 |
| E. cloacae 9570A | 0.5 | 2 | 0.125 | 0.25 | 0.125 | 0.062 |
| E. cloacae 5699 | 0.5 | 1 | 4 | 0.25 | 0.25 | 2 |
| E. cloacae 9295 | 1 | 2 | 4 | 0.5 | 0.25 | 4 |
| E. cloacae 24 | 1 | 1 | 0.5 | 0.5 | 0.125 | 0.062 |
| E. cloacae P99 | 0.062 | 0.25 | 8 | 0.062 | .062 | 8 |
| E. cloacae 214 | 0.5 | 1 | 0.5 | 0.25 | 0.125 | 2 |
| E. aerogenes 8 | 32 | 32 | 0.125 | 32 | 128 | 0.25 |
| E. aerogenes 83 | 8 | 2 | 4 | 2 | 8 | 4 |

TABLE 6-continued

| Organisms | O | L | Q | M | | Amdinocillin |
|---|---|---|---|---|---|---|
| E. aerogenes 503-478 | >128 | 8 | 16 | 4 | 4 | 8 |
| C. freundii CDC6 | 0.125 | 0.5 | 64 | 0.125 | 0.125 | 32 |
| C. freundii 8 ASM | 0.062 | 0.25 | 0.062 | 0.062 | 0.062 | 0.006 |
| C. diversus CDC 1663-72 | 0.125 | 0.5 | 0.062 | 0.062 | 0.062 | 0.062 |
| S. typhi P58A | 0.125 | 0.5 | 8 | 0.062 | 0.062 | 8 |
| S. schottmuelleri | 0.125 | 0.25 | 0.062 | 0.062 | 0.062 | 0.062 |
| P. vulgaris 100 | 8 | 32 | 1 | 8 | 0.5 | 0.5 |
| P. vulgaris 101 | 32 | 32 | 8 | 16 | 64 | 8 |
| P. vulgaris ATCC 6380 | 0.25 | 0.25 | 0.016 | 0.25 | 0.031 | 0.016 |
| P. rettgeri ATCC 9250 | 0.5 | 1 | 16 | 0.5 | 0.125 | 8 |
| P. mirabilis 503-1136 | 4 | 8 | 8 | 8 | 2 | 8 |
| P. mirabilis 620A | 4 | >128 | >128 | >128 | 64 | 8 |
| P. mirabilis 2 | 1 | 1 | 8 | 0.5 | 0.25 | 8 |
| P. mirabilis 90 | 0.5 | 2 | 0.5 | 0.5 | 0.25 | 0.25 |
| P. mirabilis 190 | 0.5 | 0.5 | 0.25 | 0.5 | 0.125 | 0.062 |
| S. marcescens 5805 | 8 | 8 | 1 | 1 | 1 | 0.5 |
| S. marcescens SM | 0.5 | 1 | 0.125 | 0.125 | 0.125 | 0.062 |
| S. marcescens S1 | 0.5 | 0.5 | 0.125 | 0.25 | 0.25 | 0.125 |
| S. marcescens S2 | 0.5 | 0.5 | 0.125 | 0.25 | 0.25 | 0.125 |
| S. marcescens S3 | 0.25 | 0.5 | 0.125 | 0.125 | 0.125 | 0.062 |
| S. marcescens S4 | 2 | 2 | 0.5 | 1 | 1 | 0.5 |
| S. marcescens S5 | 4 | 4 | 0.5 | 1 | 1 | 0.5 |
| S. marcescens S147 | 0.25 | 1 | 0.125 | 0.25 | 0.125 | 0.062 |
| S. marcescens S714 | 1 | 2 | 0.25 | 0.5 | 0.5 | 0.5 |
| P. aeruginosa B | 0.5 | 0.5 | 0.25 | 0.25 | 0.125 | 0.062 |
| P. aeruginosa Stone 130 | >128 | >128 | >128 | >128 | >128 | 128 |
| P. aeruginosa POW 151 | >128 | >128 | >128 | >128 | >128 | >128 |
| P. aeruginosa 8710 | >128 | 128 | 128 | 64 | >128 | 128 |
| P. aeruginosa 503-56 | 128 | 64 | 64 | 32 | >128 | 128 |
| P. aeruginosa 503-820 | >128 | 128 | 128 | 64 | >128 | 64 |
| P. aeruginosa 5700 | 0.5 | 2 | 0.125 | 0.125 | 0.25 | 0.062 |
| P. aeruginosa 5712 | >128 | >128 | >128 | 128 | >128 | >128 |
| P. aeruginosa 8780 | >128 | >128 | >128 | 128 | >128 | >128 |
| P. aeruginosa 6148B | >128 | 128 | 128 | 32 | >128 | 64 |
| S. faecalis C1 | 32 | 32 | 128 | 32 | >128 | 128 |
| S. pyogenes 4 | 0.5 | 0.5 | 1 | 1 | 1 | 2 |
| S. pyogenes 503-782 | 32 | 32 | 128 | 32 | >128 | 128 |
| S. pneumoniae SC | 1 | 1 | 2 | 1 | 2 | 2 |
| S. pneumoniae 6301 | 1 | 0.5 | 1 | 1 | 2 | 2 |
| S. pneumoniae 6302 | 1 | 1 | 2 | 1 | 4 | 2 |
| S. aureus Giorgio | 4 | 2 | 8 | 2 | 32 | 8 |
| S. aureus 1059B | >128 | 64 | 128 | 32 | 128 | 64 |
| S. aureus Smith | 4 | 4 | 8 | 4 | 32 | 8 |

TABLE 7

| Organisms | R | S | E | Amdinocillin |
|---|---|---|---|---|
| E. coli 257 | 0.016 | 0.25 | 0.062 | <0.008 |
| E. coli 48 | 0.016 | 0.5 | 0.062 | 0.016 |
| E. coli 4 | 2 | 4 | 4 | 2 |
| E. coli 387-1 | 2 | 2 | 4 | 2 |
| E. coli R-563 | 4 | 8 | 4 | 4 |
| E. coli 503-455 | 0.5 | 1 | 2 | 1 |
| E. coli 5152 | 4 | 8 | 8 | 16 |
| K. pneumoniae A | <0.008 | 0.5 | 0.062 | <0.008 |
| K. pneumoniae HE7 | >128 | >128 | >128 | >128 |
| K. pneumoniae 503-964 | 0.016 | 0.5 | 0.062 | 0.062 |
| K. pneumoniae 4964 | 0.5 | 0.5 | 1 | 0.062 |
| K. pneumoniae 5096 | 8 | >128 | >128 | >128 |
| K. pneumoniae 35 | 0.062 | 0.5 | 0.125 | 0.062 |
| K. pneumoniae 503-994 | 0.016 | 0.5 | 0.062 | 0.062 |
| K. pneumoniae 8357 | 0.062 | 0.5 | 0.062 | 0.062 |
| E. cloacae 6951 | 8 | 8 | 8 | 8 |
| E. cloacae 9570A | 0.062 | 1 | 0.125 | 0.125 |
| E. cloacae 5699 | 0.062 | 1 | 0.125 | 0.062 |
| E. cloacae 9295 | 0.125 | 1 | 0.25 | 0.125 |
| E. cloacae 24 | 0.25 | 1 | 0.5 | 0.5 |
| E. cloacae P99 | 0.062 | 1 | 0.125 | 0.062 |
| E. cloacae 214 | 0.5 | 4 | 0.5 | 0.5 |
| E. aerogenes 8 | 32 | 32 | 32 | 128 |
| E. aerogenes 83 | 1 | 4 | 0.5 | 4 |
| E. aerogenes 503-478 | 0.5 | 2 | 1 | 1 |
| C. freundii CDC6 | 0.062 | 0.5 | 0.125 | 0.062 |
| C. freundii 8ASM | <0.008 | 0.125 | <0.008 | <0.008 |
| C. diversus CDC 1663-72 | 0.016 | 0.5 | 0.062 | 0.062 |
| S. typhi P58A | 0.062 | 0.25 | 0.062 | 0.016 |
| S. schottmuelleri | <0.008 | 0.25 | 0.062 | <0.008 |
| P. vulgaris 100 | 2 | 8 | 8 | 0.5 |
| P. vulgaris 101 | 1 | 8 | 4 | 0.5 |
| P. vulgaris ATCC 6380 | <0.008 | 1 | 0.062 | <0.008 |
| P. rettgeri ATCC 9250 | 0.062 | 0.25 | 0.5 | <0.008 |
| P. mirabilis 503-1136 | 4 | 8 | 4 | 1 |
| P. mirabilis 620A | 64 | >128 | 128 | 32 |
| P. mirabilis 2 | 0.25 | 2 | 0.5 | 0.125 |
| P. mirabilis 90 | 0.5 | 4 | 0.5 | 0.5 |
| P. mirabilis 190 | 0.062 | 1 | 0.25 | 0.062 |
| S. marcescens 5805 | 1 | 4 | 0.5 | 1 |
| S. marcescens SM | 0.062 | 2 | 0.125 | 0.062 |
| S. marcescens S1 | 0.062 | 4 | 1 | 0.062 |
| S. marcescens S2 | 0.125 | 2 | 0.5 | 0.125 |
| S. marcescens S3 | 0.125 | 2 | 0.25 | 0.125 |
| S. marcescens S4 | 0.5 | 4 | 0.5 | 0.5 |
| S. marcescens S5 | 1 | 4 | 1 | 1 |
| S. marcescens S147 | 0.125 | 2 | 0.5 | 0.125 |
| S. marcescens S714 | 1 | 4 | 1 | 2 |
| P. aeruginosa B | 128 | >128 | >128 | >128 |
| P. aeruginosa Stone 130 | >128 | >128 | >128 | >128 |
| P. aeruginosa POW 151 | >128 | >128 | >128 | >128 |
| P. aeruginosa 8710 | >128 | >128 | >128 | >128 |
| P. aeruginosa 503-56 | >128 | >128 | >128 | >128 |
| P. aeruginosa 503-820 | 128 | >128 | >128 | >128 |
| P. aeruginosa 5700 | >128 | >128 | >128 | 128 |
| P. aeruginosa 5712 | >128 | >128 | >128 | >128 |

TABLE 7-continued

| Organisms | In Vitro MIC: μg/ml | | | |
|---|---|---|---|---|
| | R | S | E | Amdinocillin |
| P. aeruginosa 8780 | >128 | >128 | >128 | >128 |
| P. aeruginosa 6148B | 128 | >128 | >128 | 128 |
| S. faecalis C1 | 128 | 128 | 128 | >128 |
| S. pyogenes 4 | 0.5 | 0.25 | 0.5 | 1 |
| S. pyogenes 503-782 | 128 | 128 | 128 | >128 |
| S. pneumoniae SC | 0.5 | 0.5 | 0.5 | 1 |
| S. pneumoniae 6301 | 1 | 2 | 1 | 2 |
| S. pneumoniae 6302 | 1 | 1 | 1 | 2 |
| S. aureus Giorgio | 8 | 8 | 8 | 32 |
| S. aureus 1059B | 64 | 64 | 64 | 128 |
| S. aureus Smith | 8 | 8 | 8 | 16 |

TABLE 8

| Organisms | In Vitro MIC: μg/ml | | | |
|---|---|---|---|---|
| | J | Q | T | Amdinocillin |
| E. coli 257 | 0.125 | 0.062 | 0.25 | 0.062 |
| E. coli 48 | 8 | 8 | 8 | 4 |
| E. coli 4 | 0.062 | 0.062 | 0.125 | 0.062 |
| E. coli 387-1 | 0.125 | 0.062 | 0.125 | 0.062 |
| E. coli R-563 | 0.125 | 0.062 | 0.062 | 0.062 |
| E. coli 503-455 | 1 | 1 | 4 | 0.25 |
| E. coli 5152 | 16 | 64 | 32 | 8 |
| K. pneumoniae A | 0.062 | 0.062 | 0.062 | 0.062 |
| K. pneumoniae HE7 | >128 | >128 | >128 | 64 |
| K. pneumoniae 503-964 | 0.25 | 0.5 | 0.25 | 0.062 |
| K. pneumoniae 4964 | 0.5 | 4 | 0.5 | 0.062 |
| K. pneumoniae 5096 | 128 | 128 | 128 | 32 |
| K. pneumoniae 35 | 0.5 | 0.25 | 0.5 | 0.062 |
| K. pneumoniae 503-994 | 8 | 8 | 8 | 8 |
| K. pneumoniae 8357 | 4 | 4 | 16 | 8 |
| E. cloacae 6951 | 16 | 16 | 16 | 4 |
| E. cloacae 9570A | 0.5 | 0.125 | 0.5 | 0.062 |
| E. cloacae 5699 | 4 | 4 | 4 | 2 |
| E. cloacae 9295 | 4 | 4 | 8 | 4 |
| E. cloacae 24 | 0.5 | 0.5 | 0.5 | 0.062 |
| E. cloacae P99 | 8 | 8 | 8 | 8 |
| E. cloacae 214 | 1 | 0.5 | 0.5 | 2 |
| E. aerogenes 8 | 0.5 | 0.125 | 0.5 | 0.25 |
| E. aerogenes 83 | 1 | 4 | 4 | 4 |
| E. aerogenes 503-478 | 8 | 16 | 16 | 8 |
| C. freundii CDC6 | 64 | 64 | 64 | 32 |
| C. freundii 8ASM | 0.125 | 0.062 | 0.062 | 0.016 |
| C. diversus CDC 1663-72 | 0.031 | 0.062 | 0.062 | 0.062 |
| S. typhi P58A | 8 | 8 | 8 | 8 |
| S. schottmuelleri | 0.062 | 0.062 | 0.062 | 0.062 |
| P. vulgaris 100 | 8 | 1 | 8 | 0.5 |
| P. vulgaris 101 | 8 | 8 | 8 | 8 |
| P. vulgaris ATCC 6380 | 0.125 | 0.016 | 0.062 | 0.016 |
| P. rettgeri ATCC 9250 | 16 | 16 | 64 | 8 |
| P. mirabilis 503-1136 | 8 | 8 | 8 | 8 |
| P. mirabilis 620A | >128 | >128 | 128 | 8 |
| P. mirabilis 2 | 8 | 8 | 8 | 8 |
| P. mirabilis 90 | 1 | 0.5 | 1 | 0.25 |
| P. mirabilis 190 | 0.5 | 0.25 | 0.5 | 0.062 |
| S. marcescens 5805 | 1 | 1 | 4 | 0.5 |
| S. marcescens SM | 0.5 | 0.125 | 0.5 | 0.062 |
| S. marcescens S1 | 0.5 | 0.125 | 0.5 | 0.125 |
| S. marcescens S2 | 0.25 | 0.125 | 0.5 | 0.125 |
| S. marcescens S3 | 0.25 | 0.125 | 0.5 | 0.062 |
| S. marcescens S4 | 1 | 0.5 | 2 | 0.5 |
| S. marcescens S5 | 0.5 | 0.5 | 1 | 0.5 |
| S. marcescens S147 | 0.25 | 0.125 | 0.5 | 0.062 |
| S. marcescens S714 | 0.5 | 0.25 | 0.5 | 0.5 |
| P. aeruginosa B | 0.25 | 0.25 | 0.5 | 0.062 |
| P. aeruginosa Stone 130 | >128 | >128 | >128 | 128 |
| P. aeruginosa POW 151 | >128 | >128 | >128 | >128 |
| P. aeruginosa 8710 | >128 | 128 | >128 | 128 |
| P. aeruginosa 503-56 | 64 | 64 | 64 | 128 |
| P. aeruginosa 503-820 | >128 | 128 | >128 | 64 |
| P. aeruginosa 5700 | 0.5 | 0.125 | 0.5 | 0.062 |
| P. aeruginosa 5712 | >128 | >128 | >128 | >128 |
| P. aeruginosa 8780 | >128 | >128 | >128 | >128 |
| P. aeruginosa 6148B | 128 | 128 | 128 | 64 |
| S. faecalis C1 | 128 | 128 | 128 | 128 |
| S. pyogenes 4 | 4 | 1 | 4 | 2 |

TABLE 8-continued

| Organisms | In Vitro MIC: μg/ml | | | |
|---|---|---|---|---|
| | J | Q | T | Amdinocillin |
| S. pyogenes 503-782 | 128 | 128 | >128 | 128 |
| S. pneumoniae SC | 4 | 2 | 4 | 2 |
| S. pneumoniae 6301 | 1 | 1 | 2 | 2 |
| S. pneumoniae 6302 | 4 | 2 | 4 | 2 |
| S. aureus Giorgio | 8 | 8 | 8 | 8 |
| S. aureus 1059B | >128 | 128 | >128 | 64 |
| S. aureus Smith | 8 | 8 | 8 | 8 |

EXAMPLE 70

In Tables 9-14, the results of the in vivo activity against certain microorganisms of compounds I, M and N as given. The results are for the in vivo activities of these compounds alone or in combination with other antibiotic compounds such as amdinocillin, ceftriaxone, ampicillin, carbenicillin and cephalothin. The results in these Tables and the PD$_{50}$'s were determined by the procedure set forth on page 160 in Beskid et al., Antimicrobial Agents and Chemotherapy, Vol. 20, No. 2 pp. 159-167 (Aug. 1981) for "in vivo studies".

In the Tables, the fractional inhibitory concentration index (FIC) for synergistic combination of a compound of this invention (X) with known antibiotic compound (Y) is determined by the following formula:

$$FIC = \frac{PD_{50}(X \text{ combination})}{PD_{50}(X \text{ alone})} + \frac{PD_{50}(Y \text{ combination})}{PD_{50}(Y \text{ alone})}$$

An FIC of ≦0.60 is indicative of synergy. The synergy rating in the Tables is as follows:
 0.50 to 0.60 = +
 0.40 to 0.49 = + +
 0.3 to 0.39 = + + +
 <0.3 = + + + +

In the combination, the parts are parts by weight, i.e. 10 to 1 is 10 parts by weight to 1 part by weight.

EXAMPLE 71

A 100 mg injectable composition was prepared by aseptically filling in powder form 100 mg. of [2S-(2alpha,5alpha,6beta)]-6-[[[4-(1H-imidazol-1-yl-methyl)-1-piperidinyl]methylene]amino]-3,3-dimethyl-6-oxo-4-thia-1-azabicyclo[3.2.0]heptane-2-carboxylic acid into a 1 ml sterile vial. To the vial there was added sufficient sterile distilled water to fill the vial. In this manner, this composition was ready for injection.

EXAMPLE 72

A 200 mg injectable composition was prepared by aseptically filling in powder form 200 mg of [2S-(2alpha,5alpha,6beta)]-6-[[[4-[(4,5-dihydro-1H-imidazol-2-yl)methyl]-1-piperidinyl]methylene]amino]-3,3-dimethyl-7-oxo-4-thia-1-azabicyclo[3.2.0]heptane-2-carboxylic acid hydrochloride into a 1 ml sterile vial. To the vial there was added sufficient sterile distilled water to fill the vial. In this manner, this composition was ready for injection.

EXAMPLE 73

A 500 mg injectable composition was prepared by aseptically filling in powder form 500 mg of [2S-(2alpha,5alpha,6beta)]-6-[[[4-(1H-imidazol-2-yl-1-piperidinyl]methylene]amino]-3,3-dimethyl-7-oxo-4- thia-1-azabicyclo[3.2.0]heptane-2-carboxylic acid hydrochloride trihydrate in a 1 ml sterile vial. To the vial there was added sufficient sterile distilled water to fill the vial. In this manner, this composition was ready for injection.

TABLE 9

| Infecting Organism | PD$_{50}$: mg/kg sc | |
|---|---|---|
| | I | Amdinocillin |
| E. coli 257 | <0.2 | <0.025 |
| E. coli 5152 | >250 | >250 |
| E. coli 4 | 1.9 | 4.6 |
| E. aerogenes 8 | >250 | >250 |
| E. aerogenes 83 | >250 | >250 |
| S. marcescens SM | >250 | >250 |
| S. marcescens S5 | >250 | >250 |
| P. aeruginosa 503-56 | >250 | >250 |
| P. aeruginosa POW151 | 111 | 143 |
| S. aureus Smith | 61 | 69 |
| S. aureus Giorgio | >250 | >250 |
| S. pyogenes 4 | 11 | 60 |
| S. pyogenes 503-782 | 59 | 80 |
| S. pneumoniae SC | 3.6 | <2 |
| S. pneumoniae 6302 | 202 | 204 |
| S. pneumoniae 6301 | >250 | 192 |
| S. faecalis C1 | >250 | >250 |

TABLE 10

In Vivo Antibacterial Activity

| Infecting Organism | Challenge LD$_{50}$s | Number of Treatments | PD$_{50}$: mg/kg sc | | |
|---|---|---|---|---|---|
| | | | M | Amdinocillin | Ceftriaxone |
| S. aureus Smith | 48 | 2 | <5 | 22 | — |
| | 100 | 2 | 6.7 | 12 | — |
| S. pyogenes 4 | 100 | 2 | <2 | 8.1 | <2 |
| P. aeruginosa 6148B | 4.5 | 3 | <20 | — | <5 |
| | 33 | 3 | <20 | — | 8 |
| P. aeruginosa 6720 | 3511 | 2 | 29 | >250 | 14 |
| P. aeruginosa 6719 | 2249 | 3 | 34 | — | 18 |
| P. aeruginosa 8710 | 10 | 2 | 54 | >250 | — |
| | 562 | 2 | 59 | >250 | — |
| P. aeruginosa 503-56 | 4.7 | 2 | 67 | >250 | — |
| | 100 | 2 | 100 | >250 | — |
| P. aeruginosa 6799 | 48 | 2 | >250 | 117 | <10 |
| E. coli 257 | >10$^4$ | 1 | 1.5 | <1 | <1 |
| E. coli 5152 | 2717 | 2 | 134 | 84 | <5 |
| K. pneumoniae HE7 | 750 | 2 | 71 | >250 | <1 |
| E. cloacae 6951 | 562 | 2 | 15 | 18 | <1 |
| E. aerogenes 8 | 24 | 2 | 60 | >250 | 6.8 |

TABLE 11

In Vivo Antibacterial Activities

| Infecting Organism | Challenge LD$_{50}$s | Number of Treatments | PD$_{50}$: mg/kg sc | | |
|---|---|---|---|---|---|
| | | | N | Amdinocillin | Ceftriaxone |
| S. aureus Smith | 70 | 2 | 12 | 13 | 3.2 |
| S. pyogenes 4 | 3.3 | 2 | 4.3 | 11 | <2 |
| P. aeruginosa 6148B | 32 | 2 | 37 | >250 | 62 |
| P. aeruginosa 6720 | 35 | 2 | 20 | >250 | 15 |
| P. aeruginosa 6719 | 2290 | 2 | 22 | <20 | 15 |
| P. aeruginosa 8710 | >10$^4$ | 2 | 50 | >250 | 31 |
| P. aeruginosa 503-56 | 50 | 2 | 43 | >250 | >250 |
| P. aeruginosa 6799 | 71 | 2 | >250 | >250 | 16 |
| E. coli 257 | >10$^4$ | 1 | <1 | <2 | <1 |
| E. coli 5152 | 4780 | 2 | 30 | 150 | <1 |
| K. pneumoniae HE7 | 1000 | 2 | >250 | >250 | 0.39 |
| E. cloacae 6951 | 3162 | 2 | <2 | 2.5 | 0.03 |
| E. aerogenes 8 | 10 | 2 | >250 | 167 | 6.9 |
| S. marcescens S3 | 32 | 2 | <0.5 | 2.7 | 0.03 |
| S. marcescens SM | 489 | 2 | 19 | >250 | 0.2 |
| S. pneumoniae 6302 | 1000 | 1 | 78 | >250 | 0.22 |
| S. faecalis C1 | 10 | 1 | 62 | >250 | 50 |
| E. coli 387-1 | 127 | 1 | <0.2 | <0.2 | 0.09 |
| K. pneumoniae 8357 | >10$^4$ | 1 | 6.2 | 6.7 | 0.03 |
| E. cloacae 214 | 3.8 | 2 | <10 | <10 | <10 |
| C. freundii 8AMS | 1000 | 1 | 0.22 | 0.76 | 0.15 |
| S. schottmuelleri | 163 | 1 | <0.05 | 0.25 | <0.05 |
| P. vulgaris 100 | 100 | 1 | 67 | 45 | 0.05 |
| P. mirabilis 190 | 10$^4$ | 1 | 140 | 117 | 0.007 |

TABLE 12

In Vivo Activities

| Infecting Organism | Ampicillin | M | PD$_{50}$: mg/kg sc 10 + 1 Ampicillin + M | FIC 10 + 1 | Synergy rating 10 + 1 |
|---|---|---|---|---|---|
| K. pneumoniae 503-990A | 29 | 9.4 | 1.4 + 0.14 | 0.063 | + + + + |
| K. pneumoniae 39 | 9.4 | 5 | 1 + 0.1 | 0.126 | + + + + |

| Infecting Organism | Cephalothin | M | 10 + 1 Cephalothin + M | FIC 10 + 1 | Synergy rating 10 + 1 |
|---|---|---|---|---|---|
| E. coli BC5524 | >250 | 80 | 41 + 4.1 | 0.215 | + + + |
| K. pneumoniae R2296 | 69 | >250 | 34 + 3.4 | 0.507 | + |
| E. cloacae 4633 | >250 | 34 | 80 + 8 | 0.555 | + |

TABLE 13

In Vivo Activities

| Infecting Organism | Ampicillin | N | PD$_{50}$: mg/kg sc 10 + 1 Ampicillin + N | FIC 10 + 1 | Synergy rating 10 + 1 |
|---|---|---|---|---|---|
| K. pneumoniae 503-990A | 16 | 5.5 | 1.6 + 0.16 | 0.129 | + + + + |
| K. pneumoniae 39 | 18 | 18 | 1.2 + 0.12 | 0.074 | + + + + |

| Infecting Organism | Cephalothin | N | 10 + 1 Cephalothin + N | FIC 10 + 1 | Synergy rating 10 + 1 |
|---|---|---|---|---|---|
| E. coli BC5524 | >250 | 114 | >250 + >25 | >1 | NS |
| K. pneumoniae R2296 | 31 | >250 | 5.5 + 0.55 | 0.179 | + + + + |
| E. cloacae 4633 | >250 | 12 | 53 + 5.3 | 0.654 | NS |

| Infecting Organism | Challenge LD$_{50}$s | Ceftriaxone | N | 1 + 1 Ceftriaxone + | |

TABLE 13-continued

| | In Vivo Activities | | | |
|---|---|---|---|---|
| P. aeruginosa 8710 | 1738 | 41 | 50 | 28 + 28 |

TABLE 14

| Infecting Organism | Ampicillin | I | 10 + 1 Ampicillin + I | FIC 10 + 1 | Synergy rating 10 + 1 |
|---|---|---|---|---|---|
| E. coli 736 | 5 | 0.05 | 0.058 + 0.0058 | 0.128 | ++++ |
| K. pneumoniae 503-990A | (1) 58 | <2 | 3.1 + 0.31 | >0.208 | |
| | (2) 10 | <2 | <2 + >0.2 | 0.3000 | |
| K. pneumoniae 39 | 36 | 115 | <2 + <0.2 | 0.058 | ++++ |

| Infecting Organism | Cephalothin | I | 10 + 1 Cephalothin + I | FIC 10 + 1 | Synergy rating 10 + 1 |
|---|---|---|---|---|---|
| E. coli BC5524 | >250 | >250 | 87 + 8.7 | 0.383 | +++ |
| K. pneumoniae R2296 | 93 | >250 | 31 + 3.1 | 0.345 | ++++ |
| E. cloacae 4633 | >250 | 6.4 | 31 + 3.1 | 0.608 | NS |

PD$_{50}$: mg/kg sc[1]

We claim:

1. A compound of the formula

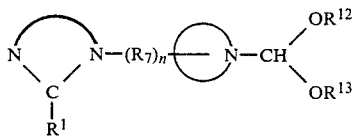

wherein n is an integer from 0 to 1;

is a saturated 5 to 7 membered heterocyclic ring containing the nitrogen as the only hetero atom in said ring, said ring being unsubstituted or substituted in one or more positions with lower alkyl;

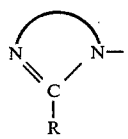

is a 5 membered heterocyclic ring having at most one additional nitrogen atom as the only hetero atom, from 0 to 2 additional double bonds, and, aside from R, either being unsubstituted or substituted in one or more positions with lower alkyl; R is selected from the group consisting of lower alkyl, nitro, hydrogen, —COOH, —(CH$_2$)$_y$—NHR$_4$, —(CH$_2$)$_y$OR$_3$ and

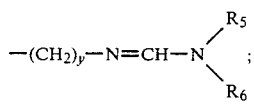

R$_3$ is hydrogen or lower alkyl, y is an integer from 0 to 4; R$_4$ is lower alkyl or an amino protecting group, R$_5$ and R$_6$ are lower alkyl or one of R$_5$ or R$_6$ is hydrogen and the other is an amino protecting group or lower alkyl; R$_{12}$ and R$_{13}$ are lower alkyl or taken together form —CH$_2$—(CH$_2$)$_x$—CH$_2$; x is an integer from 0 to 2; and R$_7$ is lower alkylene.

2. The compound of claim 1 wherein the ring

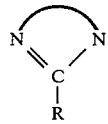

contains no additional nitrogen atoms.

3. The compound of claim 1 wherein the ring

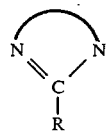

contains two unsaturated bonds.

4. The compound of claim 1 wherein the ring

is a six membered ring.

5. The compound of claim 1 wherein said compound is 4[2-imidazol-1-yl)-ethyl]-1-piperidine carboxaldehyde dimethyl acetal.

6. The compound of claim 1 wherein said compound is 4[(2-nitro-1H-imidazol-1-yl)methyl]piperidine carboxaldehyde dimethyl acetal.

* * * * *